United States Patent
Zachar et al.

(10) Patent No.: US 10,092,719 B1
(45) Date of Patent: Oct. 9, 2018

(54) CATHETER INFLATABLE CUFF PRESSURE STABILIZER

(71) Applicant: AIRWAY MEDIX S.A., Warsaw (PL)

(72) Inventors: Oron Zachar, Tel Aviv (IL); Yair Ramot, Kfar Maas (IL); Eizik Amar, Ashdod (IL)

(73) Assignee: AIRWAY MEDIX S.A., Warsaw (PL)

( * ) Notice: Subject to any disclaimer, the term of this patent is extended or adjusted under 35 U.S.C. 154(b) by 0 days.

(21) Appl. No.: 15/788,297

(22) Filed: Oct. 19, 2017

Related U.S. Application Data

(60) Provisional application No. 62/557,996, filed on Sep. 13, 2017.

(51) Int. Cl.
 *A61M 16/04* (2006.01)
 *A61M 16/01* (2006.01)
 *A61M 16/00* (2006.01)

(52) U.S. Cl.
 CPC ...... *A61M 16/044* (2013.01); *A61M 16/0003* (2014.02); *A61M 16/01* (2013.01); *A61M 2016/0027* (2013.01); *A61M 2205/3344* (2013.01); *A61M 2205/3348* (2013.01); *A61M 2210/1025* (2013.01)

(58) Field of Classification Search
 CPC .................................................. A61M 16/044
 See application file for complete search history.

(56) References Cited

U.S. PATENT DOCUMENTS

| | | |
|---|---|---|
| 3,642,005 A | 2/1972 | McGinnis |
| 3,782,363 A * | 1/1974 | Davis ..................... A61B 10/00 137/253 |
| 3,794,043 A | 2/1974 | McGinnis |
| 3,985,141 A | 10/1976 | Stanley et al. |
| 4,016,885 A | 4/1977 | Bruner |

(Continued)

FOREIGN PATENT DOCUMENTS

| | | |
|---|---|---|
| WO | 2011/133537 | 10/2011 |
| WO | 2014/090680 | 6/2014 |
| WO | 2017/153988 | 9/2017 |

OTHER PUBLICATIONS

C.V.P. Manometer product info page, downloaded Feb. 1, 2016.

(Continued)

*Primary Examiner* — Matthew Kremer
(74) *Attorney, Agent, or Firm* — Sughrue Mion, PLLC

(57) ABSTRACT

A cuff pressure stabilizer includes two or more columnar units, which include respective input columns and respective output columns disposed at least partially alongside the respective input columns. The input column of an upstream-most columnar unit is shaped so as to define an upstream-most input port, which is coupleable in fluid communication with an inflation lumen proximal port of a catheter. The output column of a downstream-most columnar unit is shaped so as to define an atmosphere port that is open to the atmosphere. The columnar units include a measurement columnar unit, which includes a plurality of pressure indicia markings distributed along the measurement columnar unit for measuring a height difference between a surface level of the liquid in the measurement output column of the measurement columnar unit and a surface level of the liquid in the measurement input column of the measurement columnar unit.

29 Claims, 18 Drawing Sheets

(56) References Cited

U.S. PATENT DOCUMENTS

| | | | |
|---|---|---|---|
| 4,064,882 A | | 12/1977 | Johnson et al. |
| 4,134,407 A | | 1/1979 | Elam |
| 4,135,494 A | | 1/1979 | Stoner et al. |
| 4,159,722 A | | 7/1979 | Walker |
| 4,182,344 A | | 1/1980 | Benson |
| 4,184,484 A | | 1/1980 | Wright et al. |
| 4,501,273 A | | 2/1985 | McGinnis |
| 4,583,917 A | | 4/1986 | Shah |
| 4,598,707 A | | 7/1986 | Agdanowski et al. |
| 4,630,606 A | | 12/1986 | Weerda et al. |
| 4,649,914 A | | 3/1987 | Kowalewski |
| 4,988,342 A | * | 1/1991 | Herweck ............ A61M 1/0013 604/321 |
| 5,098,384 A | | 3/1992 | Abrams |
| 5,218,970 A | * | 6/1993 | Turnbull ............ A61B 5/03 128/207.15 |
| 5,255,670 A | | 10/1993 | Lomholt |
| 5,279,601 A | * | 1/1994 | Lichte ............ A61M 1/0013 604/319 |
| 5,361,753 A | | 11/1994 | Pothmann et al. |
| 5,487,383 A | | 1/1996 | Levinson |
| 6,503,208 B1 | | 1/2003 | Skovlund |
| 6,647,984 B1 | | 11/2003 | O'Dea |
| 7,383,736 B2 | | 6/2008 | Esnouf |
| 8,291,768 B2 | | 10/2012 | Spiegel et al. |
| 8,397,577 B2 | | 3/2013 | Slocum, Sr. et al. |
| 2011/0220116 A1 | | 9/2011 | Lowenstein et al. |
| 2011/0247412 A1 | | 10/2011 | Scott |
| 2011/0253145 A1 | | 10/2011 | Calderoni et al. |
| 2012/0090619 A1 | | 4/2012 | Levine |
| 2012/0204884 A1 | | 8/2012 | Howard |
| 2013/0014756 A1 | | 1/2013 | Young et al. |

OTHER PUBLICATIONS

Lizy C, "Cuff Pressure of Endotracheal Tubes After Changes in Body Position in Critically Ill Patients Treated With Mechanical Ventilation," American Journal of Critical Care, pp. e1-e8, vol. 23, No. 1, Jan. 2014.

Louisiana State University ME3834 Fluid Mechanics Homework Problem_3.31, Sep. 21, 2007.

John, "Manometer," Instrumentation Today, Sep. 2011.

Duguet A et al., "Control of tracheal cuff pressure: a pilot study using a pneumatic device," Intensive Care Med. Jan. 2007;33(1):128-32.

Dwyer Instruments, Gage Fluid web page, Mar. 6, 2016 (https://web-beta.archive.Org/web/20160306163019/http://www.dwyer-inst.com/Product/Miscellaneous/Accessories/GageFluids/GageFluids) [downloaded Mar. 6, 2016].

Morrison FA, Michigan, CM3110 Homework 1 2001 Spring, Spring 2001.

"Pressure Measurement by Manometer," http://www.efm.leeds.ac.uk/CIVE/CIVE1400/Section2/Manometers.htm, downloaded Feb. 1, 2016.

Ripley G et al., "Manometer," The American Cyclopaedia—Popular Dictionary of General Knowledge. vol. 7, D. Appleton and Company, 1873.

Wilson J, "Pressure Measurement: Principles and Practice," Sensors, Jan. 1, 2003.

Sodium polytungstate data sheet, GEOLiquids, Inc., Prospect Heights, IL, Jun. 2010.

An International Search Report and a Written Opinion both dated Jun. 9, 2017, which issued during the prosecution of Applicant's PCT/IL2017/050284.

Supersonic flow, http://www-mdp.eng.cam.ac.uk/web/library/enginfo/aerothermal_dvd_only/aero/super2d/ssflow4.html, downloaded May 8, 2017.

U.S. Appl. No. 62/557,996, filed Sep. 13, 2017.
U.S. Appl. No. 62/305,567, filed Mar. 9, 2016.
U.S. Appl. No. 62/402,024, filed Sep. 30, 2016.
U.S. Appl. No. 62/405,115, filed Oct. 6, 2016.
U.S. Appl. No. 62/448,254, filed Jan. 19, 2017.

* cited by examiner

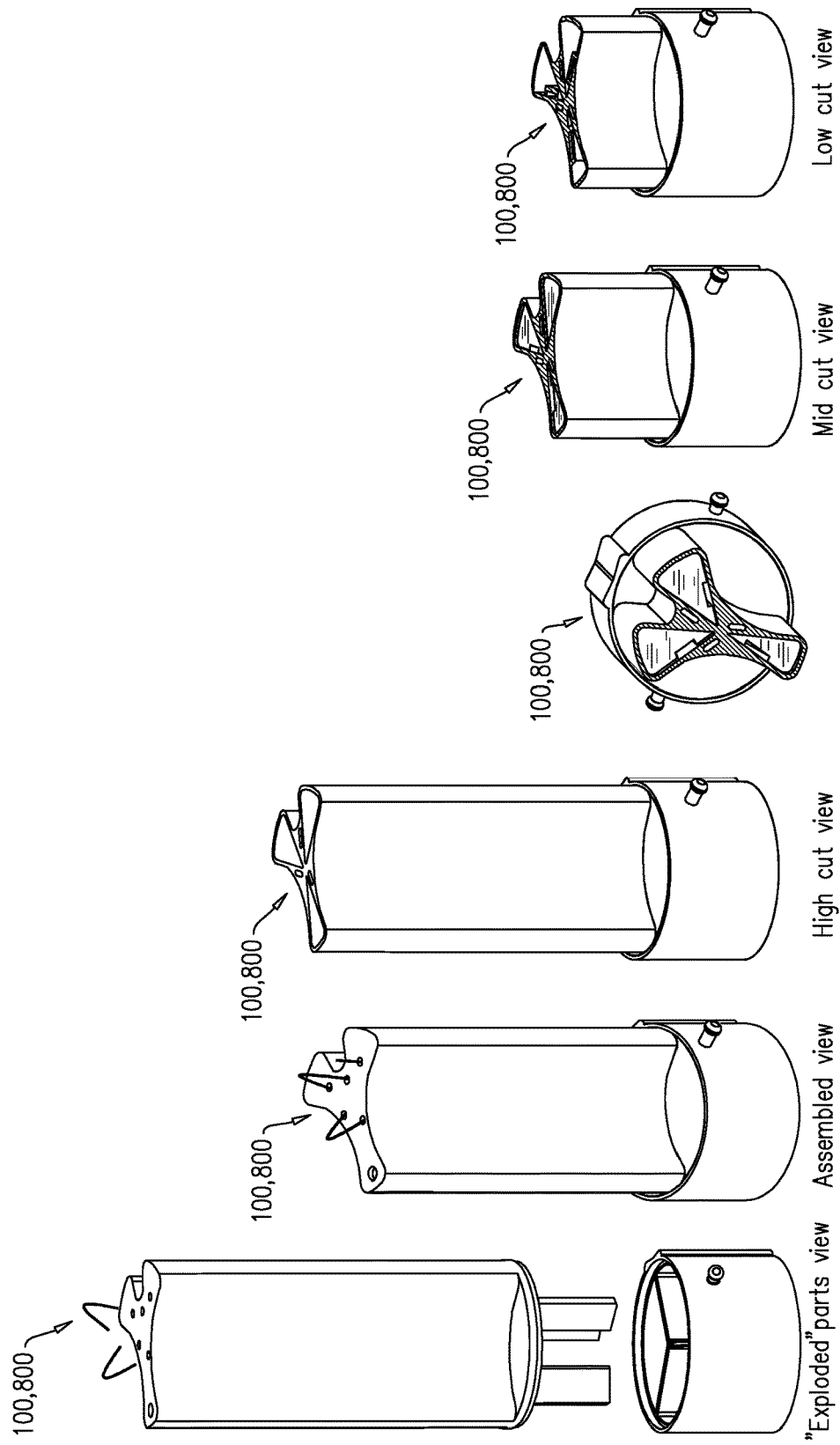

CATHETER INFLATABLE CUFF PRESSURE STABILIZER

CROSS-REFERENCE TO RELATED APPLICATIONS

The present application claims the benefit of U.S. Provisional Application 62/557,996, filed Sep. 13, 2017, which is assigned to the assignee of the present application and is incorporated herein by reference.

FIELD OF THE APPLICATION

The present invention relates generally to medical suction catheter systems, and specifically to endotracheal tube inflatable cuff manometers.

BACKGROUND OF THE APPLICATION

Suction catheters are commonly used to aspirate tracheobronchial fluids in patients ventilated with endotracheal tube (ETT) and tracheostomy tube devices.

Some ETTs comprise an inflatable cuff, which forms a seal against the tracheal wall. This seal prevents gases from leaking past the cuff and allows positive pressure ventilation. Desired safe inflatable cuff pressure is in the range of 23-27 cm H2O, with optimal pressure about 25 cm H2O. Pressure above 30 cm H2O can cause irritation to the surrounding tracheal tissue. Extended duration of such high cuff pressure can interfere with oxygen flow to the tissue, causing tissue necrosis and a substantial wound. Low cuff balloon pressure, typically below 20 cm H2O, compromises the cuff sealing performance, and allows leakage into the lungs of subglottic fluids descending from above the balloon.

The external surface of inflatable cuffs is in communication with the ventilation pressure of the lungs. The pressure of the inflatable cuff cycles with the ventilation cycle. When an artificially-ventilated patient is also anesthetized, the plastic of the inflatable cuff absorbs the nitrous oxide (N2O) gas used in anesthesia, which increases pressure in the cuff.

In current clinical settings of intensive care patients, changes of body positioning lead to significant changes in cuff pressure in the range of 10-50 cm H2O, i.e., out of the safe range of 20-30 cm H2O, and certainly out of the desired range of 23-27 cm H2O. See, for example, Lizy C et al., "Cuff pressure of endotracheal tubes after changes in body position in critically ill patients treated with mechanical ventilation," Am J Crit Care. 2014 January; 23(1):e1-8.

Therefore, there is a need to safely maintain the inflatable cuff pressure is in the range of 23-27 cm H2O, optimally about 25 cm H2O, and to avoid extended periods of pressure above 30 cm H2O. In particular, there is a need to suppress the fluctuations of pressure in clinical settings caused by patient change of body positions.

Currently, the most common practiced approach for ETT cuff pressure management is manual monitoring (using a manometer) and adjustment of cuff pressure, which contributes to ICU staff workload. It has been shown that up to eight manual adjustments of cuff pressure are required daily to maintain recommended cuff pressure ranges. Even so, the cuff pressure is uncontrolled during the long time periods between manual cuff adjustments. In addition, the manometer must be connected to and disconnected from the ETT cuff for each pressure measurement, which allows a small amount of air to escape from the ETT cuff. Still further, many conventional ETT manometers lose calibration relatively quickly.

Prior art cuff pressure regulators can be divided into two groups: (a) large bedside non-disposable expensive electric pump and electronic pressure monitors; and (b) small and light disposable non-electric limited-pressure reservoir compartments that must be filled manually. Use of disposable devices both prevents cross-contamination between patients and obviates the need for costly sterilization processes between patients. Moreover, the compactness of the disposable devices allows them to be attached on the ETT circuit and not occupy bedside space and an electric power cable connection.

SUMMARY OF THE APPLICATION

Some applications of the present invention provide a cuff pressure stabilizer for use with a catheter, such as a tracheal ventilation tube that comprises inflatable cuff, an inflation lumen, and an inflation lumen proximal port. The cuff pressure stabilizer is configured to provide automatic pressure regulation of the inflatable cuff, while simultaneously continuously displaying the pressure in the inflatable cuff. The cuff pressure stabilizer comprises two or more columnar units, which are disposed at least partially alongside one another. Providing two or more (e.g., three) columnar units, rather than a single columnar unit, provides allows the cuff pressure stabilizer to have a shorter height.

There is therefore provided, in accordance with an application of the present invention, a cuff pressure stabilizer for use in contact with the atmosphere of the Earth and for use with a catheter having an inflatable cuff, an inflation lumen, and an inflation lumen proximal port, the cuff pressure stabilizer including:

two or more columnar units, which:
include (a) respective input columns and (b) respective output columns, wherein the respective output columns (i) are disposed at least partially alongside the respective input columns, and (ii) are in fluid communication with the respective input columns when the cuff pressure stabilizer is in an operational state, and
include (a) an upstream-most columnar unit and (b) a downstream-most columnar unit;
a liquid; and
a gas,
wherein the input column of the upstream-most columnar unit is shaped so as to define an upstream-most input port, which is coupleable in fluid communication with the inflation lumen proximal port of the catheter,
wherein the output column of the downstream-most columnar unit is shaped so as to define an atmosphere port that is open to the atmosphere when the cuff pressure stabilizer is in the operational state,
wherein the output column of the upstream-most columnar unit is disposed at least partially alongside the output column of the downstream-most columnar unit,
wherein when the cuff pressure stabilizer is in the operational state, the two or more columnar units are arranged so as to define a fluid communication path from the upstream-most input port, to the input column of the upstream-most columnar unit, to the output column of the upstream-most columnar unit, to the input column of the downstream-most columnar unit, to the output column of the downstream-most columnar unit, and to the atmosphere port,
wherein the columnar units include a measurement columnar unit, which includes a plurality of pressure indicia markings distributed along the measurement columnar unit for measuring a height difference between a surface level of the liquid in the measurement output column of the measurement columnar unit and a surface level of the liquid in the measurement input column of the measurement columnar unit, wherein when the cuff pressure stabilizer is in the operational state and is oriented in an aligned orientation in which the pressure indicia markings reflect, to within 1 cm H2O, pressure of gas at the upstream-most input port at least in a target-pressure range of 23 to 27 cm H2O:

the output columns have respective average target-pressure inner cross-sectional areas, each of the average target-pressure inner cross-sectional areas measured in a horizontal plane at all axial locations along the respective output column that correspond to respective pressures of the gas at the upstream-most input port in the target-pressure range, and each of the average target-pressure inner cross-sectional areas is between 0.5 and 4 cm2, and wherein when the cuff pressure stabilizer is in the operational state and is oriented in the aligned orientation and the pressure of the gas at the upstream-most input port falls in the target-pressure range:

the liquid is contained at least partially in the output columns, and the gas is contained at least partially in the input column of the downstream-most columnar unit and at least partially in the output column of the upstream-most columnar unit.

For some applications:

the measurement input column of the measurement columnar unit is shaped so as to define a measurement fluid reservoir, the measurement output column is shaped so as to define an inlet that is disposed entirely within the measurement fluid reservoir, when the cuff pressure stabilizer is in the operational state, the measurement input column is in fluid communication with the inlet of the measurement output column via the measurement fluid reservoir, and when the cuff pressure stabilizer is in the operational state and the gas at the upstream-most input port is at atmospheric pressure, a volume of the liquid in the measurement fluid reservoir is greater than a volume of the liquid in the measurement output column.

For some applications, w en the cuff pressure stabilizer is in the operational state and is oriented in the aligned orientation:

an average inner cross-sectional area of the measurement fluid reservoir, measured in the horizontal plane between upper and lower height end-points, equals at least 200% of an average relevant-pressure inner cross-sectional area of the measurement output column, measured in the horizontal plane at all axial locations along the measurement output column that correspond to respective pressures of the gas at the upstream-most input port in a relevant-pressure range of 0 to 30 cm H2O.

the upper height end-point is at a height that corresponds to a pressure of the gas at the upstream-most input port of atmospheric pressure, and the lower height end-point is at a height of the highest point at which there is fluid communication between the measurement output column and the measurement input column.

For some applications, a distance between a highest point of the measurement output column and a lowest point of the measurement fluid reservoir is between 12 and 24 cm, when the cuff pressure stabilizer is oriented in the aligned orientation.

For some applications, the distance between the highest point of the measurement output column and the lowest point of the measurement fluid reservoir is between 15 and 22 cm, when the cuff pressure stabilizer is oriented in the aligned orientation.

For some applications, a volume of the measurement fluid reservoir is at least 2 cc, such as at least 4 cc.

For some applications, the cuff pressure stabilizer is configured such that when the cuff pressure stabilizer is in the operational state and the gas at the upstream-most input port is at atmospheric pressure, a volume of the liquid in the measurement fluid reservoir is less than a volume of the measurement output column.

For some applications, the cuff pressure stabilizer is configured such that when the cuff pressure stabilizer is in the operational state and the gas at the upstream-most input port is at atmospheric pressure, for at least one of the columnar units, a volume of the liquid in the input column of the columnar unit is less than a volume of the output column of the columnar unit.

For some applications, the cuff pressure stabilizer is configured such that when the cuff pressure stabilizer is in the operational state and the gas at the upstream-most input port is at atmospheric pressure, for all of the columnar units, respective volumes of the liquid in the respective input columns of the columnar units are less than respective volumes of the respective output columns of the columnar units.

For some applications:

the columnar units include, in addition to the measurement columnar unit, one or more non-measurement columnar units, and at least one of the average target-pressure inner cross-sectional areas of the one or more output columns of the one or more non-measurement columnar units equals at least 120% of the average target-pressure inner cross-sectional area of the measurement output column, when the cuff pressure stabilizer is oriented in the aligned orientation.

For some applications, the at least one of the average target-pressure inner cross-sectional areas of the one or more output columns of the one or more non-measurement columnar units equals at least 150% of the average target-pressure inner cross-sectional area of the measurement output column, when the cuff pressure stabilizer is oriented in the aligned orientation.

For some applications, each of the average target-pressure inner cross-sectional areas of the one or more output columns of the one or more non-measurement columnar units equals at least 120% of the average target-pressure inner cross-sectional area of the measurement output column, when the cuff pressure stabilizer is oriented in the aligned orientation.

For some applications, each of the average target-pressure inner cross-sectional areas of the one or more output columns of the one or more non-measurement columnar units equals at least 150% of the average target-pressure inner cross-sectional area of the measurement output column, when the cuff pressure stabilizer is oriented in the aligned orientation.

For some applications, when the cuff pressure stabilizer is in the operational state, the liquid in the one or more non-measurement columnar units is obscured from viewing from outside the cuff pressure stabilizer at least in the target-pressure range.

For some applications, the input column of the measurement columnar unit contains a portion of the gas at all pressures of the gas at the upstream-most input port in a relevant-pressure range between 0 and 30 cm H2O, when the cuff pressure stabilizer is in the operational state and is oriented in the aligned orientation.

For some applications, the input column of the measurement columnar unit is filled with the portion of the gas at all pressures of the gas at the upstream-most input port in the relevant-pressure range, when the cuff pressure stabilizer is in the operational state and is oriented in the aligned orientation.

For some applications, the output column of the upstream-most columnar unit is disposed at least partially alongside the output column of the downstream-most columnar unit for a distance of at least 3 cm, measured vertically when the cuff pressure stabilizer is oriented in the aligned orientation.

For some applications, the downstream-most columnar unit is configured as the measurement columnar unit.

For some applications, the volume of the liquid is between 3 and 30 cc. For some applications, the volume of the liquid is between 4 and 20 cc.

For some applications, for each of the output columns, an inner cross-sectional area thereof, measured in the horizontal plane, is between 0.5 and 4 cm2 at all axial locations along the output column that correspond to respective pressures of the gas at the upstream-most input port in the target-pressure range, when the cuff pressure stabilizer is in the operational state and is oriented in the aligned orientation. For some applications, each of the average target-pressure inner cross-sectional areas is at least 1 cm2. For some applications, each of the average target-pressure inner cross-sectional areas is no more than 3 cm2.

For some applications:
the two or more columnar units include three or more columnar units, which include (i) the upstream-most columnar unit, (ii) the downstream-most columnar unit, and (iii) at least an intermediate columnar unit, and
when the cuff pressure stabilizer is in the operational state, the three or more columnar units are arranged so as to define the fluid communication path from the upstream-most input port, to the input column of the upstream-most columnar unit, to the output column of the upstream-most columnar unit, to the input column of the intermediate columnar unit, to the output column of the intermediate columnar unit, to the input column of the downstream-most columnar unit, to the output column of the downstream-most columnar unit, and to the atmosphere port.

For some applications:
the cuff pressure stabilizer is shaped so as to define an intermediate-column input port between the output column of the upstream-most columnar unit and the input column of the intermediate columnar unit, and a downstream-column input port between the output column of the intermediate columnar unit and the input column of the downstream-most columnar unit, and
the cuff pressure stabilizer further includes one or more sealing elements that block fluid communication through the intermediate-column input port and through the downstream-column input port when the cuff pressure stabilizer is in a non-operational state.

For some applications, the two or more columnar units include exactly two columnar units, which include the upstream-most columnar unit and the downstream-most columnar unit.

For some applications, the cuff pressure stabilizer includes one or more sealing elements, and when the cuff pressure stabilizer is in a non-operational state, the one or more sealing elements block fluid communication between at least one adjacent pair of the columnar units.

For some applications, the input column of the measurement columnar unit is shaped so as to define a measurement-column input port, and the cuff pressure stabilizer further includes one or more sealing elements that block fluid communication through the measurement-column input port when the cuff pressure stabilizer is in a non-operational state.

For some applications, the pressure indicia markings are distributed evenly throughout at least the target-pressure range.

For some applications, when the cuff pressure stabilizer is oriented in the aligned orientation:
the output columns have respective average low-pressure inner cross-sectional areas,
each of the average low-pressure inner cross-sectional areas is measured in the horizontal plane at all axial locations along the respective output column that correspond to respective pressures of the gas at the upstream-most input port in a low pressure range of between 5 and 15 cm H2O, and
for each of the output columns, the average target-pressure inner cross-sectional area thereof equals at least 200% of the average low-pressure inner cross-sectional area thereof.

For some applications, a central longitudinal axis of the measurement output column is perpendicular to the horizontal plane, when the cuff pressure stabilizer is oriented in the aligned orientation.

For some applications, a central longitudinal axis of the measurement output column is not perpendicular to the horizontal plane, when the cuff pressure stabilizer is oriented in the aligned orientation.

For some applications:
the cuff pressure stabilizer further includes an inflation lumen proximal port connector, which is shaped to form an air-tight seal with the inflation lumen proximal port of the catheter, and
when the cuff pressure stabilizer is in the operational state, the upstream-most input port is in fluid communication with the inflation lumen proximal port connector such that the upstream-most input port is coupleable in fluid communication with the inflation lumen proximal port of the catheter via the inflation lumen proximal port connector.

For some applications, the inflation lumen proximal port connector includes a male conical fitting with a taper. For some applications, the taper is at least a 5% taper. For some applications, the taper is a 6% taper, and the male conical fitting with the 6% taper complies with International Standard ISO 594-1:1986.

For some applications, the liquid has a density of between 0.8 and 1.2 g/cm3 at 4 degrees Celsius at 1 atm. For some applications, the density is between 0.95 and 1.05 at 4 degrees Celsius at 1 atm. For some applications, the liquid includes at least 50% water by volume.

For some applications, the catheter is a tracheal ventilation tube, and the cuff pressure stabilizer is for use with the tracheal ventilation tube.

For some applications, the cuff pressure stabilizer does not include any membranes that block a fluid path between the upstream-most input port and the atmosphere port when the cuff pressure stabilizer is in the operational state. Alternatively or additionally, for some applications, the cuff pressure stabilizer does not include a spring for measuring the pressure of the gas at the inflation lumen proximal port connector.

For some applications, the cuff pressure stabilizer is for use with a pole, and the cuff pressure stabilizer includes a coupling element selected from the group consisting of:

a hook or a loop, which is configured to automatically orient the measurement output column in the aligned orientation when hung from a hook of the pole, and a squeezing coupler that is coupleable to a vertical or horizontal portion of the pole.

For some applications, a system is provided that includes the cuff pressure stabilizer and the catheter, which includes the inflatable cuff, the inflation lumen, and the inflation lumen proximal port. For some applications, the inflatable cuff has a volume of between 5 and 25 cc and a largest cross-sectional area, measured in the horizontal plane, of between 2 and 9 cm2 when inflated to an inflation pressure of 25 cm H2O when not constrained and in the atmosphere; and when the cuff pressure stabilizer is oriented in the aligned orientation, the measurement-column inner cross-sectional area equals between 20% and 80% of the middle cross-sectional area of the inflatable cuff.

There is further provided, in accordance with an application of the present invention, a method for use in contact with the atmosphere of the Earth and for use with a catheter having an inflatable cuff, an inflation lumen, and an inflation lumen proximal port, the method including:

providing a cuff pressure stabilizer, which includes (A) two or more columnar units, which (a) include (i) respective input columns and (ii) respective output columns, wherein the respective output columns (1) are disposed at least partially alongside the respective input columns, and (2) are in fluid communication with the respective input columns when the cuff pressure stabilizer is in an operational state, and (b) include (i) an upstream-most columnar unit and (ii) a downstream-most columnar unit; (B) a liquid; and (C) a gas; and coupling the upstream-most input port in fluid communication with the inflation lumen proximal port of the catheter, wherein the input column of the upstream-most columnar unit is shaped so as to define an upstream-most input port, which is coupleable in fluid communication with the inflation lumen proximal port of the catheter, wherein the output column of the downstream-most columnar unit is shaped so as to define an atmosphere port that is open to the atmosphere when the cuff pressure stabilizer is in the operational state, wherein the output column of the upstream-most columnar unit is disposed at least partially alongside the output column of the downstream-most columnar unit, wherein when the cuff pressure stabilizer is in the operational state, the two or more columnar units are arranged so as to define a fluid communication path from the upstream-most input port, to the input column of the upstream-most columnar unit, to the output column of the upstream-most columnar unit, to the input column of the downstream-most columnar unit, to the output column of the downstream-most columnar unit, and to the atmosphere port, wherein the columnar units include a measurement columnar unit, which includes a plurality of pressure indicia markings distributed along the measurement columnar unit for measuring a height difference between a surface level of the liquid in the measurement output column of the measurement columnar unit and a surface level of the liquid in the measurement input column of the measurement columnar unit, wherein when the cuff pressure stabilizer is in the operational state and is oriented in an aligned orientation in which the pressure indicia markings reflect, to within 1 cm H2O, pressure of gas at the upstream-most input port at least in a target-pressure range of 23 to 27 cm H2O:

the output columns have respective average target-pressure inner cross-sectional areas, each of the average target-pressure inner cross-sectional areas measured in a horizontal plane at all axial locations along the respective output column that correspond to respective pressures of the gas at the upstream-most input port in the target-pressure range, and each of the average target-pressure inner cross-sectional areas is between 0.5 and 4 cm2, and wherein when the cuff pressure stabilizer is in the operational state and is oriented in the aligned orientation and the pressure of the gas at the upstream-most input port falls in the target-pressure range:

the liquid is contained at least partially in the output columns, and the gas is contained at least partially in the input column of the downstream-most columnar unit and at least partially in the output column of the upstream-most columnar unit.

The present invention will be more fully understood from the following detailed description of embodiments thereof, taken together with the drawings, in which:

BRIEF DESCRIPTION OF THE DRAWINGS

FIGS. 11A-F are schematic illustrations of still another cuff pressure stabilizer, in accordance with an application of the present invention.

DETAILED DESCRIPTION OF APPLICATIONS

Figure 1:
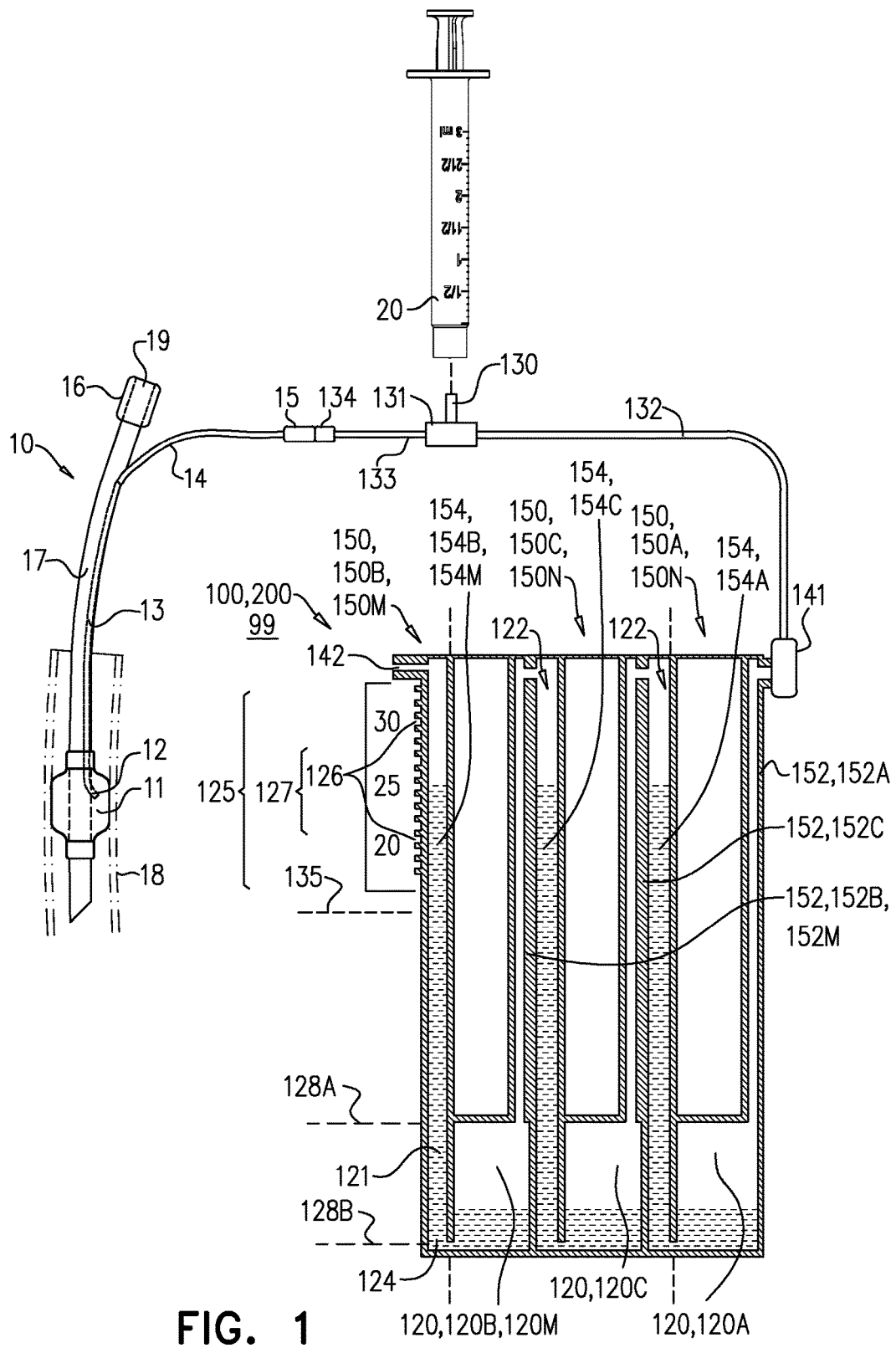
FIG. 1 is a schematic illustration of a cuff pressure stabilizer for use with a catheter, in accordance with an application of the present invention.

FIGS. 1-12C are schematic illustrations of respective configurations of a cuff pressure stabilizer 100 for use with a catheter 10, such as a tracheal ventilation tube, in accordance with respective applications of the present invention. Cuff pressure stabilizer 100 is for use in contact with the atmosphere 99 (i.e., ambient air) of the Earth. FIG. 1 also shows (a) catheter 10, which is not a component of cuff pressure stabilizer 100, (b) an external inflation source 20, such as a syringe, which is not a component of cuff pressure stabilizer 100, and (c) connector tubes, described hereinbelow, which are optionally a component of cuff pressure stabilizer 100 (and may be removably or permanently coupled to cuff pressure stabilizer 100).

Catheter 10 (e.g., the tracheal ventilation tube) comprises an inflatable cuff 11, an inflation lumen 13, and an inflation lumen proximal port 15. Inflatable cuff 11 may comprise, for example, a balloon, and is typically mounted on catheter 10 near a distal end of the tracheal ventilation tube, e.g., within 3 cm, such as within 1 cm, of the distal end. Inflatable cuff 11 typically comprises a nearly non-compliant material. A "balloon," as used in the present application, including the claims, is an inflatable flexible bag, having any level of elasticity, including nearly non-elastic. Typically, inflatable cuff 11 has a volume of between 5 and 20 cc, depending on the size of catheter 10. Catheter 10 typically further comprises a cuff inflation lumen distal port 12, a tracheal ventilation tube ventilation port 16, a tracheal ventilation tube ventilation lumen 17, and a tracheal ventilation tube ventilator connection 19. For some applications, catheter 10 further comprises an inflating tube 14, which couples inflation lumen 13 in fluid communication with inflation lumen proximal port 15. Catheter 10 is schematically shown inserted into a trachea 18. Inflatable cuff 11 is inflatable into sealing contact with the inner surface of trachea 18. As used in the present application, including in the claims, a "tracheal ventilation tube" comprises an endotracheal tube (ETT) or a tracheostomy tube.

Reference is still made to FIGS. 1-12C. Cuff pressure stabilizer 100 comprises:
two or more columnar units 150, each comprising a pair of input/output columns 152/154, such that columnar units 150:
comprise (a) respective input columns 152 and (b) respective output columns 154; respective output columns 154 (i) are disposed at least partially alongside respective input columns 152, and (ii) are in fluid communication with respective input columns 152 when cuff pressure stabilizer 100 is in an operational state, such as described hereinbelow with reference to FIGS. 4A-B and 12A-C, and
include (a) an upstream-most columnar unit 150A and (b) a downstream-most columnar unit 150B;
a liquid 121;
a gas 122, typically air; and
typically, a casing 110.

An input column 152A of upstream-most columnar unit 150A is shaped so as to define an upstream-most input port 141, which is coupleable in fluid communication with inflation lumen proximal port 15 of catheter 10. An output column 154B of downstream-most columnar unit 150B is shaped so as to define an atmosphere port 142 that is open to atmosphere 99 when cuff pressure stabilizer 100 is in the operational state.

For some applications, cuff pressure stabilizer 100 further comprises an inflation lumen proximal port connector 134, which is shaped to form an air-tight seal with inflation lumen proximal port 15 of catheter 10. For these applications, when cuff pressure stabilizer 100 is in the operational state, upstream-most input port 141 is in fluid communication with inflation lumen proximal port connector 134 such that upstream-most input port 141 is coupleable in fluid communication with inflation lumen proximal port 15 of catheter 10 via the inflation lumen proximal port connector 134. For some of these applications, inflation lumen proximal port connector 134 comprises a male conical fitting with a taper. For some applications, the taper is at least a 5% taper. For some applications, the taper is a 6% taper, and the male conical fitting with the 6% taper complies with International Standard ISO 594-1:1986, which is the standard for connections to conventional inflation lumen proximal ports of tracheal ventilation tubes.

For some applications, the volume of liquid 121 is at least 3 cc, such as at least 4 cc, at least 10 cc, or at least 12 cc, and no more than 30 cc, e.g., no more than 20 cc. e.g., between 3 and 30 cc, such as between 4 and 20 cc.

An output column 154A of upstream-most columnar unit 150A is typically disposed at least partially alongside output column 154B of downstream-most columnar unit 150B, such as described in more detail hereinbelow with reference to FIGS. 1-12C and 6. One or more of output columns 154 may be radially surrounded by one or more others of the output columns, such that output column 154A of upstream-most columnar unit 150A is disposed at least partially alongside output column 154B of downstream-most columnar unit 150B.

When cuff pressure stabilizer 100 is in the operational state, the two or more columnar units 150 are arranged so as to define a fluid communication path from upstream-most input port 141, to input column 152A of upstream-most columnar unit 150A, to output column 154A of upstream-most columnar unit 150A, to an input column 152B of downstream-most columnar unit 150B, to output column 154B of downstream-most columnar unit 150B, and to atmosphere port 142.

For some applications, such as described hereinbelow, one or more of input columns 152 are shaped so as to define respective wider fluid reservoirs 120, which are disposed at the bottom of their respective measurement input columns 152 when cuff pressure stabilizer 100 is oriented in an aligned orientation, also as described hereinbelow. For these applications, references made to the surface level of liquid 121 in an input column 152 are to be understood as referring interchangeably to the narrower upper portion of the input column and/or the wider fluid reservoir.

Columnar units 150 include a measurement columnar unit 150M, which comprises a plurality of pressure indicia markings 126. Pressure indicia markings 126 may be distributed along either a measurement output column 154M of measurement columnar unit 150M or a measurement input column 152M of measurement columnar unit 150M. Typically, pressure indicia markings 126 are distributed along measurement output column 154M of measurement columnar unit 150M. Pressure indicia markings 126 correspond to height difference between the surface level of liquid 121 in measurement output column 154M and the surface level of liquid 121 in measurement input column 152M. There is a correspondence between pressure and the height difference between the surface level of liquid 121 in measurement output column 154M and the surface level of liquid 121 in measurement input column 152M. Pressure indicia markings 126 thus serve to represent pressure measurement. Typically, casing 110 has pressure indicia markings 126, as shown in the figures, in which case pressure indicia markings 126 are distributed along measurement output column 154M or measurement input column 152M by being distributed on casing 110 alongside measurement output column 154M or measurement input column 152M, as the case may be. Alternatively, measurement output column 154M itself or measurement input column 152M itself, as the case may be, has pressure indicia markings 126. For some applications, pressure indicia markings 126 are distributed evenly throughout at least target-pressure range 127, described hereinbelow.

For some applications, as shown, downstream-most columnar unit 150B is configured as measurement columnar unit 150M, while for other applications, another of columnar units 150 is configured as measurement columnar unit 150M. Optionally, more than one of columnar units 150 are configured as respective measurement columnar units 150M, such as to allow viewing of the pressure reading from more than one side of cuff pressure stabilizer 100.

Typically, pressure indicia markings 126 correspond to the difference between the height of the surface level of liquid 121 in measurement output column 154M and the height of the surface level of liquid 121 in measurement input column 152M (such as the height of the surface level of liquid 121 in measurement fluid reservoir 120M, if provided). As the liquid surface descends in measurement input column 152M (such as in measurement fluid reservoir 120M, if provided), the liquid surface ascends in measurement output column 154M, although typically not by the same changes in heights because of differing cross-sectional areas between the input and the output columns. Therefore, the spacing of pressure indicia markings 126 depends in part on the shape and volume of measurement input column 152M (and measurement fluid reservoir 120M, if provided). For example, the spacing of pressure indicia markings 126 between 25 and 26 cm H2O may be different from the spacing of pressure indicia markings 126 between 26 and 27 cm H2O. In addition, for example, the wider the measurement fluid reservoir 120M, the greater the spacing of pressure indicia markings 126.

When in the operational state, cuff pressure stabilizer 100 is used in an aligned orientation (hereinbelow, the "aligned orientation") in which pressure indicia markings 126 reflect, to within 1 cm H2O (i.e., with no error or an error of no more than 1 cm H2O), pressure gas 122 at upstream-most input port 141 (and also at inflation lumen proximal port connector 134, if provided) at least in a target-pressure range 127 of 23 to 27 cm H2O. A fully marked scale range 125 typically extends both above and below target-pressure range 127. The pressure is read by comparing the surface level of liquid 121 in measurement output column 154M with pressure indicia markings 126 (or, for other configurations, such as mentioned above, by comparing the surface level of liquid 121 in measurement input column 152M with pressure indicia markings 126). A central longitudinal axis of measurement output column 154M may or may not be perpendicular to a horizontal plane 135, when cuff pressure stabilizer 100 is oriented in the aligned orientation. As used in the present application, including in the claims, "horizontal" means horizontal with respect to the Earth, i.e., perpendicular to a vertical line directed to the center of gravity of the Earth, e.g., as ascertained using a plumb-line.

For some applications, for each of output columns 154, an inner cross-sectional area thereof, measured in horizontal plane 135, is between 0.25 and 4 cm2, typically between 0.5 and 4 cm2, such as at least 1 cm2 and/or no more than 3 cm2, at all axial locations along the output column 154 that correspond to respective pressures of gas 122 at upstream-most input port 141 (and also at inflation lumen proximal port connector 134, if provided) in target-pressure range 127, when cuff pressure stabilizer 100 is oriented in the aligned orientation.

Typically, when cuff pressure stabilizer 100 is in the operational state and is oriented in the aligned orientation and the pressure of gas 122 at upstream-most input port 141 (and also at inflation lumen proximal port connector 134, if provided) falls in target-pressure range 127:

liquid 121 is contained at least partially in output columns 154, and gas 122 is contained at least partially in input column 152B of downstream-most columnar unit 150B and at least partially in output column 154A of upstream-most columnar unit 150A.

Reference is again made to FIGS. 1-12C. For some applications, columnar units 150 include, in addition to measurement columnar unit 150M, one or more non-measurement columnar units 150N (for example, columnar units 150A and 150C, as shown in FIG. 1). For some applications, when cuff pressure stabilizer 100 is in the operational state, liquid 121 in the one or more non-measurement columnar units 150N is obscured from viewing from outside cuff pressure stabilizer 100 at least in target-pressure range 127.

Reference is again made to FIGS. 1-12C. Typically, measurement input column 152M contains a portion of gas 122 at all pressures of gas 122 at upstream-most input port 141 (and also at inflation lumen proximal port connector 134, if provided) in a relevant-pressure range between 0 and 30 cm H2O, when cuff pressure stabilizer 100 is in the operational state and is oriented in the aligned orientation. Typically, measurement input column 152M is filled with the portion of gas 122 at all pressures of gas 122 at upstream-most input port 141 (and also at inflation lumen proximal port connector 134, if provided) in the relevant-pressure range, when cuff pressure stabilizer 100 is in the operational state and is oriented in the aligned orientation.

Reference is again made to FIGS. 1-12C. For some applications, the two or more columnar units 150 comprise three or more columnar units 150, which include (i) upstream-most columnar unit 150A, (ii) downstream-most columnar unit 150B, and (iii) at least an intermediate columnar unit 150C. When cuff pressure stabilizer 100 is in the operational state, the three or more columnar units 150 are arranged so as to define the fluid communication path from upstream-most input port 141, to input column 152A of upstream-most columnar unit 150A, to output column 154A of upstream-most columnar unit 150A, to an input column 152C of intermediate columnar unit 150C, to an output column 154C of intermediate columnar unit 150C, to input column 152B of downstream-most columnar unit 150B, to output column 154B of downstream-most columnar unit 150B, and to atmosphere port 142.

For other applications, the two or more columnar units 150 comprise exactly two columnar units 150, which include upstream-most columnar unit 150A and downstream-most columnar unit 150B (configuration not shown).

Reference is still made to FIGS. 1-12C. For some applications, measurement input column 152M is shaped so as to define a measurement fluid reservoir 120M, which is disposed at the bottom of measurement input column 152M when cuff pressure stabilizer 100 is oriented in the aligned orientation. Measurement output column 154M is shaped so as to define an inlet 124 that is disposed entirely within measurement fluid reservoir 120M. When cuff pressure stabilizer 100 is in the operational state, measurement input column 152M is in fluid communication with inlet 124 of measurement output column 154M via measurement fluid reservoir 120M. As can be seen, gas 122 partially fills measurement fluid reservoir 120M. When cuff pressure stabilizer 100 is in the operational state and gas 122 at upstream-most input port 141 (and also at inflation lumen proximal port connector 134, if provided) is at atmospheric pressure (0 cm H2O), a volume of liquid 121 in input column 152 is greater than a volume of liquid 121 in measurement output column 154, e.g., the volume of liquid 121 in input column 152 equals at least 150% (e.g., at least 300%, such as at least 500%) of the volume of liquid 121 in measurement output column 154.

Typically, when cuff pressure stabilizer 100 is in the operational state and is oriented in the aligned orientation:
  an average inner cross-sectional area of measurement fluid reservoir 120M, measured in horizontal plane 135 between upper and lower height end-points 128A and 128B, equals at least 200% (e.g., at least 300%, such as at least 400%) of an average relevant-pressure inner cross-sectional area of measurement output column 154M, measured in horizontal plane 135 at all axial locations along measurement output column 154M that correspond to respective pressures of gas 122 at upstream-most input port 141 (and also at inflation lumen proximal port connector 134, if provided) in a relevant-pressure range of 0 to 30 cm H2O,
  upper height end-point 128A is at a height of the surface level of liquid 121 in measurement input column 152M that corresponds to a pressure of gas 122 at upstream-most input port 141 (and also at inflation lumen proximal port connector 134, if provided) equal to atmospheric pressure (0 cm H2O, which denotes the reference ambient air pressure of atmosphere 99), and
  lower height end-point 128B is at a height of the highest point at which there is fluid communication between measurement output column 154M and measurement input column 152M (via inlet 124).

For some applications, a distance between a highest point of measurement output column 154M and a lowest point of measurement input column 152M is between 12 and 24 cm, such as between 15 and 22 cm, when cuff pressure stabilizer 100 is oriented in the aligned orientation. For some applications, a volume of measurement fluid reservoir 120M is at least 2 cc, such as at least 4 cc, at least 6 cc, at least 8 cc, at least 10 cc, or at least 20 cc.

For some applications, in addition to measurement input column 152M, one or more of the other input columns 152 are shaped so as to define respective fluid reservoirs 120 (120A, 120B, and 120C), such as shown in FIG. 1-9. Each of these fluid reservoirs 120 may have the above-described properties of measurement fluid reservoir 120M with respect to elements of its respective columnar unit. Although all of fluid reservoirs 120 are shown as having the same initial level of liquid 121 in the resting state, this is not necessarily the case. (In the configurations shown in the figures, fluid reservoir 120B of downstream-most input column 152B corresponds with measurement fluid reservoir 120M.) For other applications, such as described hereinbelow with reference to FIGS. 10A-B, only measurement input column 152M comprises a fluid reservoir.

For some applications, cuff pressure stabilizer 100 is configured such that when cuff pressure stabilizer 100 is in the operational state and gas 122 at upstream-most input port 141 (and also at inflation lumen proximal port connector 134, if provided) is at atmospheric pressure, for at least one of columnar units 150, a volume of liquid 121 in input column 152 of the columnar unit 150 (e.g., in fluid reservoir 120 of the columnar unit 150, if provided) is less than a volume of output column 154 of the columnar unit 150. As the pressure of gas 122 at upstream-most input port 141 (and also at inflation lumen proximal port connector 134, if provided) is increased above atmospheric pressure, some of liquid 121 is pushed from each of input columns 152 to the corresponding output column 154. The higher the pressure, the more liquid 121 that is pushed. As a result, cuff pressure stabilizer 100 is arranged such that if inflatable cuff 11 is squeezed to a high threshold pressure (e.g., greater than 36 cm H2O), further squeezing of inflatable cuff 11 releases gas 122 bubbles through liquid 121 in at least one of output columns 154, thereby preventing the pressure from further increasing within inflatable cuff 11.

For some applications, for all of columnar units 150, respective volumes of liquid 121 in respective input columns 152 (e.g., in respective fluid reservoirs 120 of the columnar units, if provided) are less than respective volumes of output columns 154 of the columnar units. As a result, the equilibrium balance between the columnar units is not disturbed by the valve release event (because the same amount of gas 122 moves between all columns, if all of reservoirs 120 are of the same volume and all lower height end-points 128B are at the same level in all columnar units 150, such as shown in many of the figures).

For applications in which a volume of liquid 121 in measurement input column 152M (e.g., in measurement fluid reservoir 120M, if provided) is less than a volume of measurement output column 154M, the bubbling occurs in measurement output column 154M and out of atmosphere port 142 into atmosphere 99. In other words, if inflatable cuff 11 is squeezed to a high threshold pressure at which most available liquid 121 in measurement input column 152M (e.g., measurement fluid reservoir 120M, if provided) has moved into measurement output column 154M, further squeezing of inflatable cuff 11 releases gas 122 bubbles through liquid 121 in measurement output column 154M and into fluid communication with atmosphere 99, and thus prevents the pressure from further increasing within inflatable cuff 11. If the initial volume of liquid 121 in measurement fluid reservoir 120M were instead greater than the volume of measurement output column 154M, some liquid 121 would spill out of measurement output column 154M and prevent continued accurate function of cuff pressure stabilizer 100. This arrangement effectively serves the same function as a maximum pressure release valve.

(The above-mentioned volumes of output columns 154, including measurement output column 154M, are to be understood as meaning the volumes of liquid 121 that output columns are able to contain, rather than the volume of liquid 121 actually in output columns 154 at any point in time, e.g., when gas 122 at upstream-most input port 141 (and also at inflation lumen proximal port connector 134, if provided) is at atmospheric pressure.)

Figure 2A:
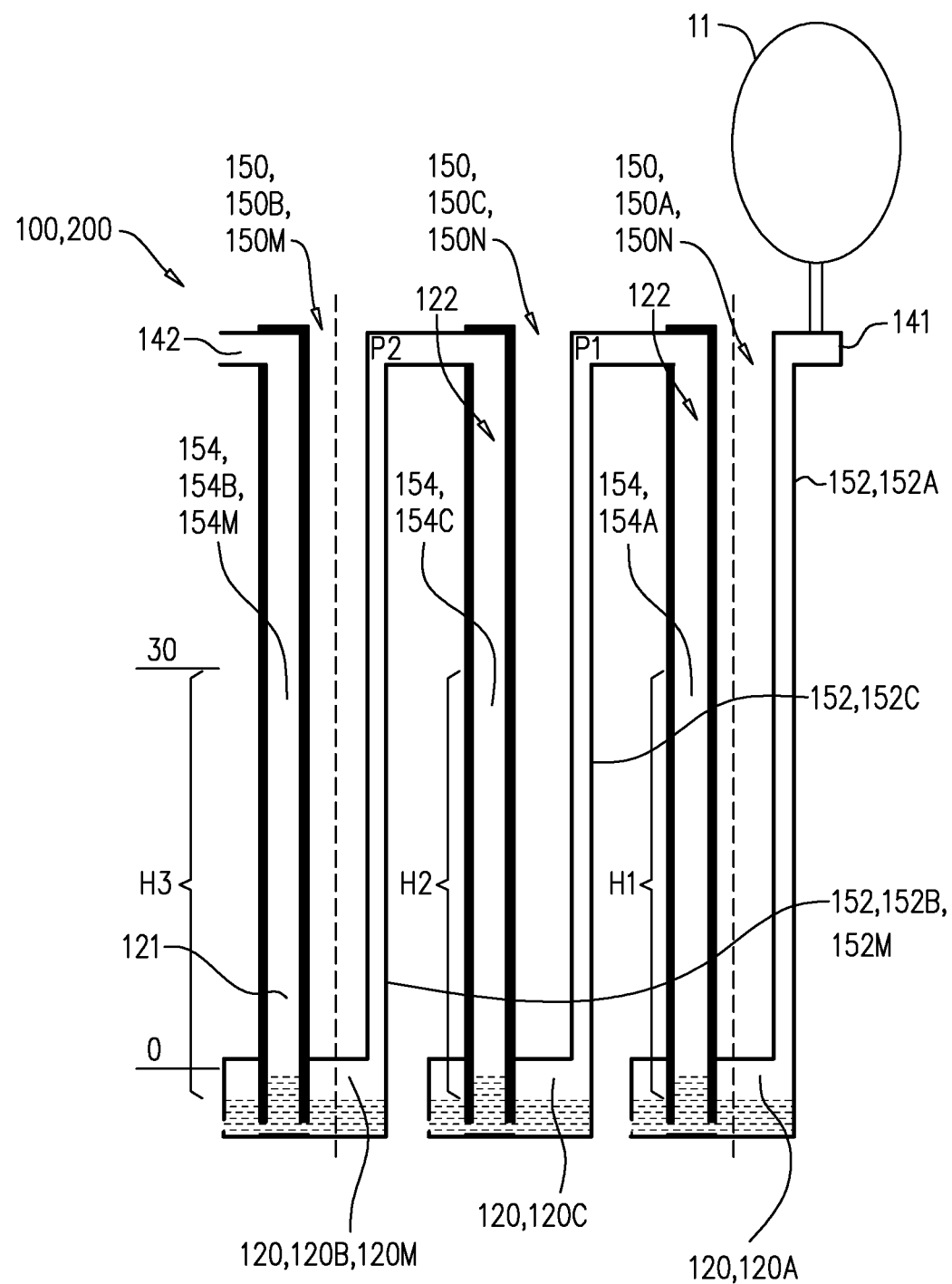
FIGS. 2A-B are additional schematic illustrations of the cuff pressure stabilizer of FIG. 1 in resting and pressurized states, respectively, in accordance with an application of the present invention.
Figure 2B:
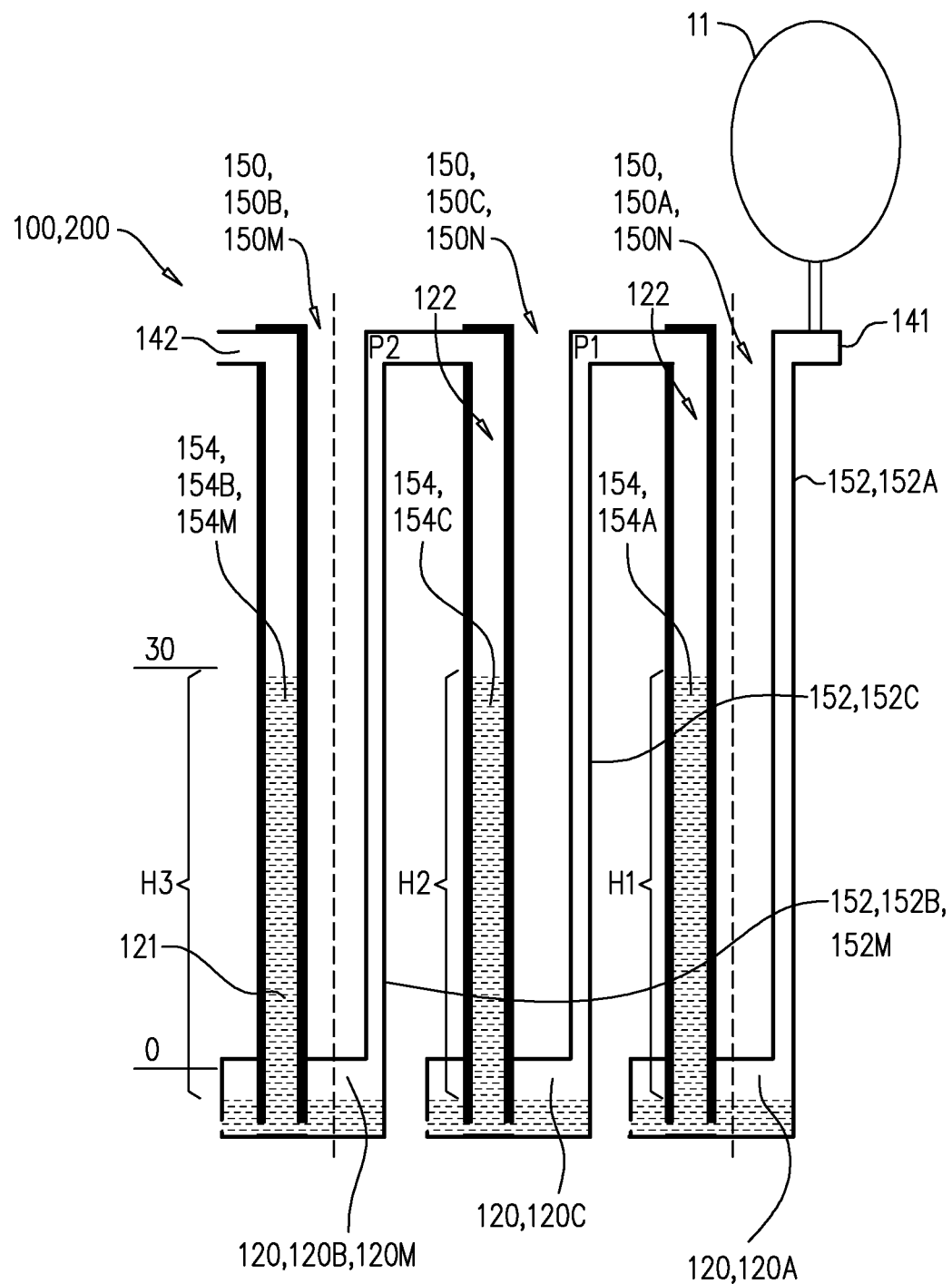
Figure 3:
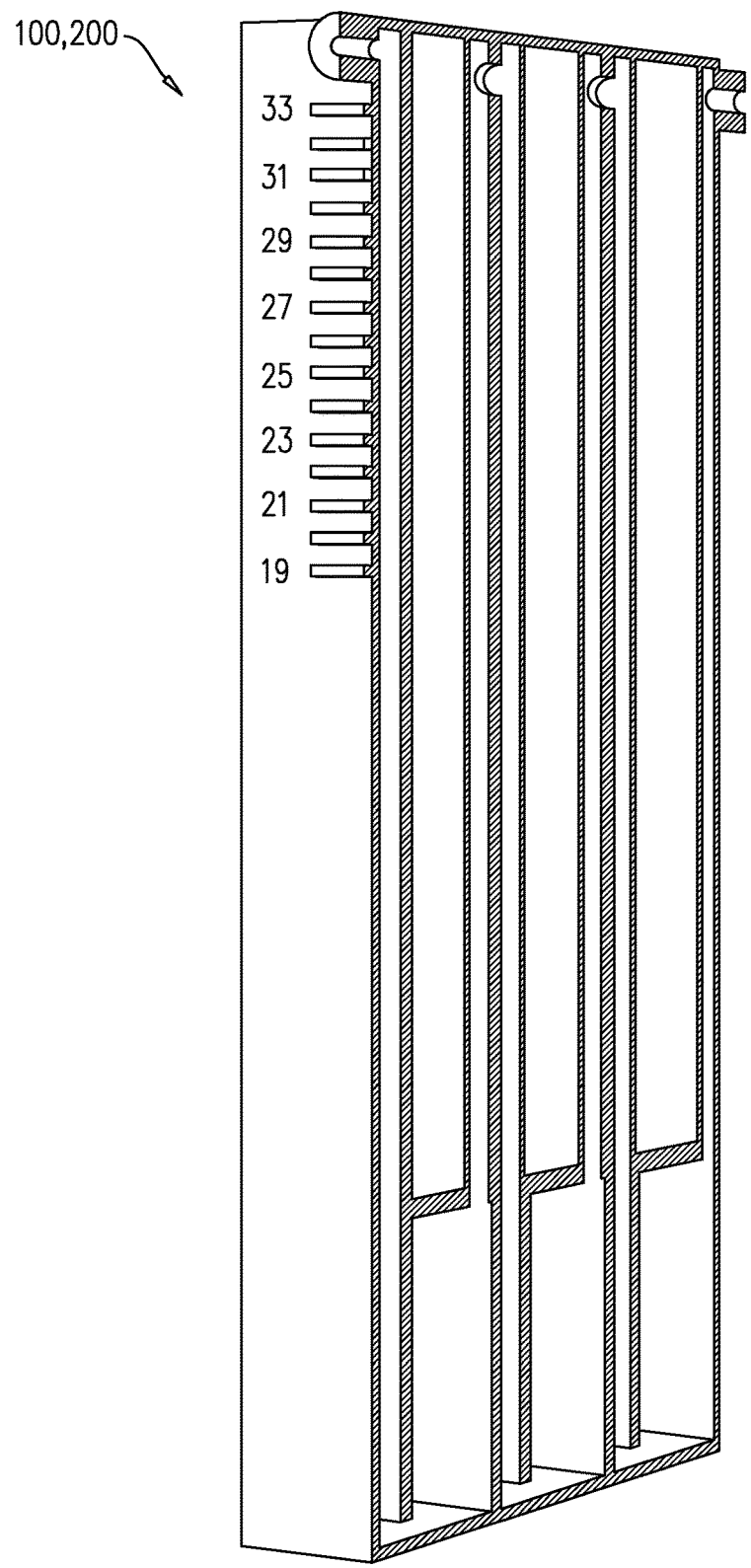
FIG. 3 which is yet another schematic illustration of the cuff pressure stabilizer of FIG. 1, in accordance with an application of the present invention.

Reference is now made to FIGS. 1-4B, which are schematic illustrations of a cuff pressure stabilizer 200, in accordance with respective applications of the present invention. Cuff pressure stabilizer 200 is one implementation of cuff pressure stabilizer 100, described herein with reference to FIGS. 1-12C, and may implement any of the features thereof. Reference is also made to FIG. 3, which is schematic illustration of cuff pressure stabilizer 200, in accordance with an application of the present invention.

In cuff pressure stabilizer 200, at least one of (typically, all of) the average target-pressure inner cross-sectional areas of the one or more output columns 154 of the one or more non-measurement columnar units 150N equals between 95% and 105%, typically 100%, of the average target-pressure inner cross-sectional area of measurement output column 154M, when cuff pressure stabilizer 100 is oriented in the aligned orientation.

Reference is again made to FIGS. 1-12C, including to FIGS. 2A-B, which are additional schematic illustrations of cuff pressure stabilizer 200 in resting and pressurized states, respectively, in accordance with an application of the present invention. FIG. 2A (as well as FIGS. 4A-B, 7A, and 8A, described hereinbelow in more detail) shows cuff pressure stabilizer 100 in a resting state of the operational state. In this resting state, the pressure of atmosphere 99 is 1 atm. inflatable cuff 11 is inflated to 1 atm, and the surface level of liquid 121 is the same in all output columns 154 and is equal to the surface level of liquid 121 in the corresponding input columns 152 of units 150.

As the pressure increases in inflatable cuff 11 from the resting state to a pressurized state of the operational state, such as shown in FIG. 2B (as well as in FIGS. 1, 5A-B. 6, 7B, 8B, 9, and 10B), liquid 121 rises in output columns 154, and goes down in fluid reservoirs 120 (or input columns 152 of the non-measurement columnar units in the configuration described hereinbelow with reference to FIGS. 10A-B). The resulting height differences between output columns 154 and their respective fluid reservoirs 120 are labeled H1, H2, and H3 for output column 154A of upstream-most columnar unit 150A, output column 154C of intermediate columnar unit 150C, and output column 154B of downstream-most columnar unit 150B, respectively.

In order to simplify the calculations, in the following discussion, as well as similar discussions hereinbelow, gas 122 is assumed to be non-compressible. Any slight compressibility of gas 122 under practical pressure conditions does not have a significant effect on the accuracy of the pressure measurements provided by cuff pressure stabilizer 100, i.e., the compressibility will lead to deviations which are of magnitude less than 1 cm H2O in the relevant pressure range of under 40 cm H2O.

Cuff pressure stabilizer 100 can be characterized by the following principles:

for a given liquid 121 and structure of the columns, there is a one-to-one correspondence between each pressure in inflatable cuff 11 and the sum of the height differences in output columns 154 (e.g., H1, H2, and H3) (the correspondence function depends upon the density of liquid 121 and the geometry of the columns), and the volume displaced in each of columnar units 150 is identical, and equals the volume displaced from inflatable cuff 11.

Reference is again made to FIGS. 2A-B. As mentioned above, in cuff pressure stabilizer 200 in some configurations, at least one of (typically, all of) the average target-pressure inner cross-sectional areas of the one or more output columns 154 of the one or more non-measurement columnar units 150N equals between 95% and 105%, typically 100%, of the average target-pressure inner cross-sectional area of measurement output column 154M, when cuff pressure stabilizer 100 is oriented in the aligned orientation.

For example, assume the following parameters:
liquid 121 comprises water,
cuff pressure stabilizer 200 comprises exactly three columnar units 150 and exactly three corresponding output columns 154,
cuff pressure stabilizer 200 comprises exactly three fluid reservoirs 120, each of which has a cross-sectional area of 5 cm2, measured in horizontal plane 135,
the cross-sectional area of the three output columns 154 are equal to one another, and equal 1 cm2, and
the pressure in inflatable cuff 11 is 30 cm H2O.
Then:

$$H1+H2+H3=30 \text{ cm} \quad \text{(Equation 1)}$$

$$H1=H2=H3=10 \text{ cm} \quad \text{(Equation 2)}$$

Since H1=10 cm, a pressure P1 of gas 122 in output column 154A of upstream-most columnar unit 150A (and input column 152C of intermediate columnar unit 150C) equals 20 cm H2O (i.e., 10 cm H2O less than the pressure of 30 cmH2O of inflatable cuff 11, as reflected at upstream-most input port 141 (and also at inflation lumen proximal port connector 134, if provided)). Since H2=10 cm, a pressure P2 of gas 122 in output column 154C of intermediate columnar unit 150C (and input column 152B of downstream-most columnar unit 150B) equals 10 cm H2O.

The surface level of liquid 121 in each of the three fluid reservoirs 120 goes down:

$$10 \text{ cm3}/5 \text{ cm2}=2 \text{ cm} \quad \text{(Equation 3)}$$

Hence, the distance between (a) the surface level of liquid 121 in measurement output column 154M when the pressure at upstream-most input port 141 (and also at proximal port connector 134, if provided) is 0 cm H2O and (b) the surface level of liquid 121 in measurement output column 154M when the pressure at upstream-most input port 141 (and also at proximal port connector 134, if provided) is 30 cm H2O equals 10 cm−2 cm=8 cm. Therefore, the vertical distance between 1 cm H2O pressure indicia markings 126 equals:

$$(10 \text{ cm}-2 \text{ cm})/30=\sim 0.267 \text{ cm} \quad \text{(Equation 4)}$$

In order to tolerate a maximum pressure of 36 cm H2O, measurement output column 154M must have a height of at least about 10 cm (0.267*36=~10) above the resting liquid level at zero pressure (i.e., ambient pressure).

Providing two or more (e.g., three) columnar units 150, rather than a single columnar unit, allows cuff pressure stabilizer 100 to have a shorter height. However, providing two or more columnar units 150 results in smaller separation between pressure indicia markings 126 on measurement columnar unit 150M. In order to provide adequate scale resolution (e.g., greater than 2.5 mm between adjacent 1-cm-H2O pressure indicia markings 126) in the range of interest of pressures less than 40 cm H2O, the inventors have found that it is generally best to provide no more than three columnar units 150, i.e., only two or three columnar units 150; nevertheless, the scope of the present invention is not limited to only two or three columnar units 150, and cuff pressure stabilizer 100 may comprise more than three columnar units 150, such as four or five columnar units 150, or even more.

Typically, when cuff pressure stabilizer 100 is oriented in the aligned orientation:
output columns 154 have respective average target-pressure inner cross-sectional areas, each of the average target-pressure inner cross-sectional areas measured in horizontal plane 135 at all axial locations along the respective output column 154 that correspond to respective pressures of gas 122 at upstream-most input port 141 (and also at inflation lumen proximal port connector 134, if provided) in target-pressure range 127 (even though there are typically no pressure indicia markings 126 on the non-measurement output columns), and each of the average target-pressure inner cross-sectional areas is between 0.25 and 4 cm, typically between 0.5 and 4 cm2, such as at least 1 cm2 and/or no more than 3 cm2.

As a result of this relatively large cross-sectional area, cuff pressure stabilizer 100 regulates (i.e., reduces fluctuations) the pressure of gas 122 at upstream-most input port 141 (and thus in inflatable cuff 11) at least for changes of gas volume in the range of 0-2 cc, in addition to measuring the pressure, i.e., the movement of the liquid surface level in wide output columns 154 simultaneously serves to measure the pressure and to regulate pressure variations associated with changes of gas volume in the range of 0-2 cc in inflatable cuff 11. By contrast, conventional manometers, which are designed to be dedicated measurement devices, only measure the pressure, without substantially affecting the pressure, as it is ideally and commonly the goal of measurement devices to not affect the measured target, by having a volume in the manometer that is not significant compared to the volume of the target measurement system. For a given cuff of initial gas volume V, as the squeezing of inflatable cuff 11 by trachea 18 increases such that the available gas volume decreases, the volume of the gas in inflatable cuff 11 decreases by some fraction equal to the change in V divided by V because the cuff is nearly non-compliant. For endotracheal tubes without external regulation, this decrease in volume of the inflatable cuff results in an increase in pressure of the gas within the system, including within the inflatable cuff, since the gas contained in the cuff has no significant external volume to move into, in accordance with the ideal gas law; the opposite occurs when the level of squeezing on the cuff by the trachea decreases.

In experiments conducted by the inventors using a single-column cuff pressure stabilizer, such as described in International Application PCT/IL2017/050284, filed Mar. 8, 2017, which published as PCT Publication WO 2017/153988 and is assigned to the assignee of the present application and is incorporated herein by reference, the inventors found that, for real endotracheal tube cuff balloons of volumes around 10 cc, each 0.1 cc decrease in volume in the inflatable cuff resulted in about a 1 cm H2O increase in pressure in the system and the cuff, and each 0.1 cc increase in volume in the inflatable cuff resulted in about a 1 cm H2O decrease in pressure in the system and the cuff. This is a surprising significant departure from the ideal non-compliant gas law calculation which would predict a 0.01 cc volume change per 1 cm H2O pressure change. The inventors thus concluded that real endotracheal tube cuff balloons are in fact semi-compliant. Therefore, the mitigation volumes should be calculated based on the experimental finding. In clinical practice, the pressure in ETT inflatable cuffs generally varies +/−10 cm H2O from the typically target pressure of 25 cm H2O, i.e., varies between 15 and 35 cm H2O. Based on the above-mentioned experimental data, the inventors appreciated that the volume in ETT inflatable cuffs generally varies by +/−1 cc (+/−10 cm H2O times 0.1 cc/cm H2O), i.e., a total range of 2 cc, and, among a broader spectrum of patients, the volume of ETT inflatable cuffs generally varies by +/−20 cm H2O from the typical target pressure of 25 cm H2O, i.e., a total range of at least 4 cc.

The inventors appreciated that to the extent that cuff pressure stabilizer 100 is able to offset the changes in volume in inflatable cuff 11, the pressure changes are also offset, thereby stabilizing the pressure in inflatable cuff 11. Cuff pressure stabilizer 100 is able to offset the changes in volume in inflatable cuff 11 because of the relatively large cross-sectional area of output columns 154 at target-pressure range 127, e.g., 23-27 cm H2O.

Reference is again made to FIGS. 2A-B. For example, assume that:

liquid 121 comprises water,
cuff pressure stabilizer 100 comprises exactly three columnar units 150 and exactly three corresponding output columns 154,
the average target-pressure inner cross-sectional area of each of output columns 154 in target-pressure range 127 is 1 cm2,
cuff pressure stabilizer 100 comprises exactly three fluid reservoirs 120, each of which has a cross-sectional area of 5 cm2, measured in horizontal plane 135,
pressure indicia markings 126 are spaced at 2.67-mm intervals, and
the initial pressure in inflatable cuff 11 is 25 cm H2O.

A decrease in volume of inflatable cuff 11 of 1 cc (caused by increased squeezing by the trachea) would displace:

from inflatable cuff 11 the excess 1 cc of gas 122 into fluid reservoir 120A,
a corresponding 1 cc of liquid 121 out of fluid reservoir 120A into output column 154A.
a corresponding 1 cc of gas 122 into fluid reservoir 120C,
a corresponding 1 cc of liquid 121 out of fluid reservoir 120C into output column 154C,
a corresponding 1 cc of gas 122 into fluid reservoir 120B, and
a corresponding 1 cc of liquid 121 out of fluid reservoir 120B into output column 154B (which, in this configuration, serves as measurement output column 154M).

The additional 1 cc of water in each of output columns 154 would fill an additional 1 cc of each of output columns 154, raising the surface level of liquid 121 in each of output columns 154 by 1 cm, and thus the pressure in inflatable cuff 11 (as indicated by pressure indicia markings 126 spaced at 0.267 cm) by about 3.75 cm H2O, from 25 cm H2O to 28.75 cm H2O.

For a real inflatable cuff having a volume of 10 cc without attachment of the regulation system, a decrease in volume of inflatable cuff 11 of 1 cc would have resulted in an increase of the cuff pressure gas by about 10 cm H2O, based on the inventors' experimental data, i.e., the integration of the pressure regulator with catheter 10 (a tracheal ventilation tube) results in a factor of 2.6 (=10/3.75) suppression of the pressure change, resulting in the pressure regulation described herein. Importantly, in the clinical context, the pressure remains within the clinically tolerated range of 20-30 cm H2O.

The fluctuation suppression factor is larger for larger cross-sections of output columns 154. The inventors believe that the typical range of cuff balloon pressure fluctuations of about +/−20 cm H2O is primarily caused by confining volume changes of inflatable cuff 11 in the range of +/−2 cc. Therefore, cuff pressure stabilizer 100 typically comprises output columns 154 with cross-sectional areas sufficiently large such that adding 2 cc of liquid would raise the surface level of liquid 121 between pressure indicia markings 126 of less than 10 cm H2O, typically less than 5 cm H2O.

The above example with output columns 154 with cross-sectional areas of 1 cm2 resulted in pressure indicia markings 126 of 1 cm H2O separated by 2.67 mm, such that a 2 cc volume change would result in surface liquid level movement between pressure indicia markings 126 by 7.5 cm H2O. Therefore, a pressure increase of 7.5 cm H2O from an initial setting of 25 cm H2O results in a pressure of 32.5 cm H2O, which is slightly above an upper limit of 30 cm H2O. Providing output columns 154 with cross-sectional areas of greater than 1 cm2 reduces the maximum pressure resulting from such a pressure increase. Typically, cross-sections larger than 2 cm2 are not helpful.

More generally, the change in pressure in inflatable cuff 11 within target-pressure range 127, resulting from a change in volume of inflatable cuff 11, when liquid 121 does not comprise pure water (e.g., comprises a solution, an oil, or another constituent), i.e., has a density (d) other than 1 g/cm3 at 4 degrees Celsius at 1 atm. For every calculation done for water, the spacing of pressure indicia markings 126 is changed simply by the factor 1/d.

Figure 4A:
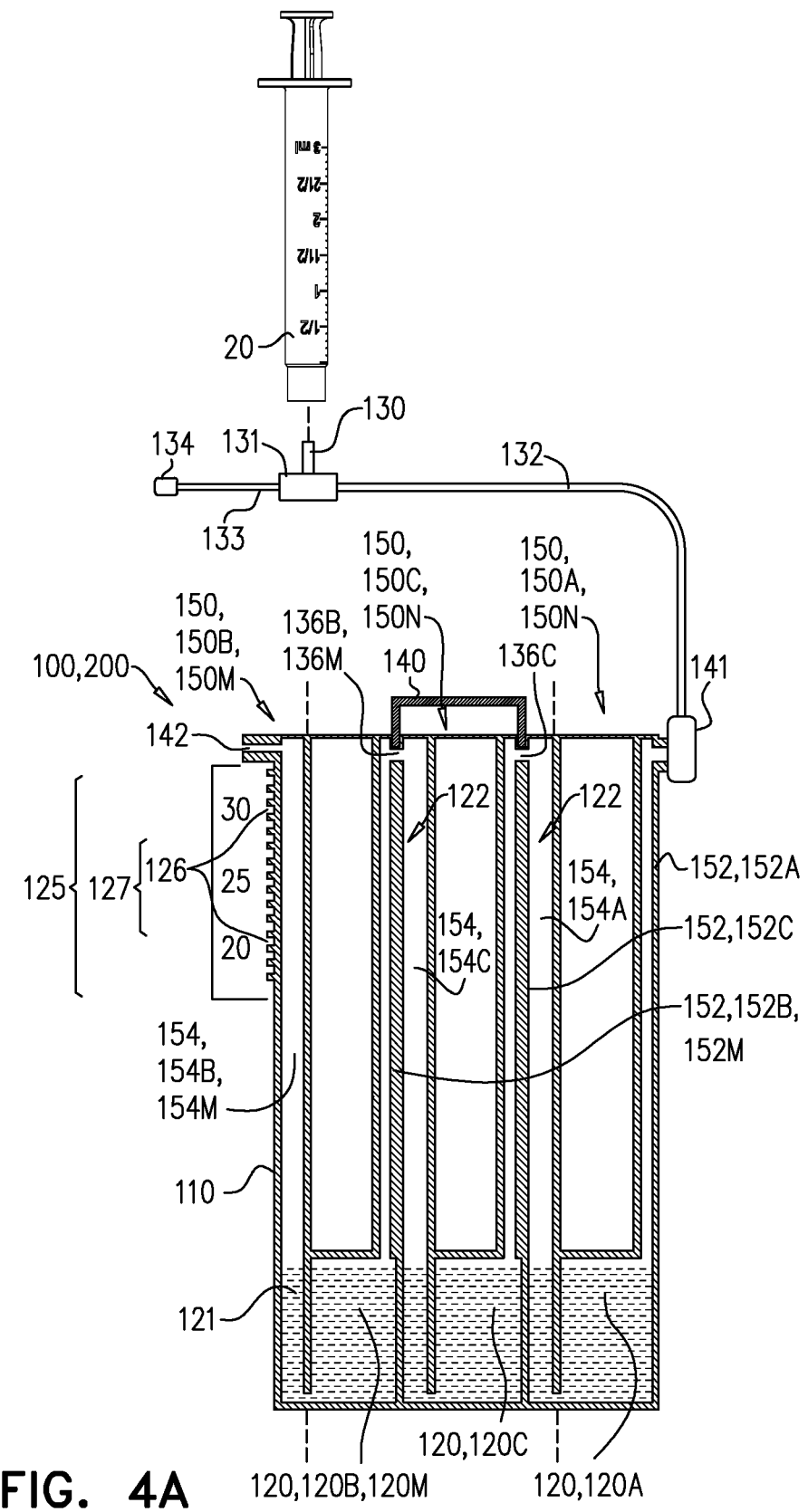
FIGS. 4A-B are schematic illustrations of the cuff pressure stabilizer of FIG. 1 in operational and non-operational states, in accordance with an application of the present invention.
Figure 4B:
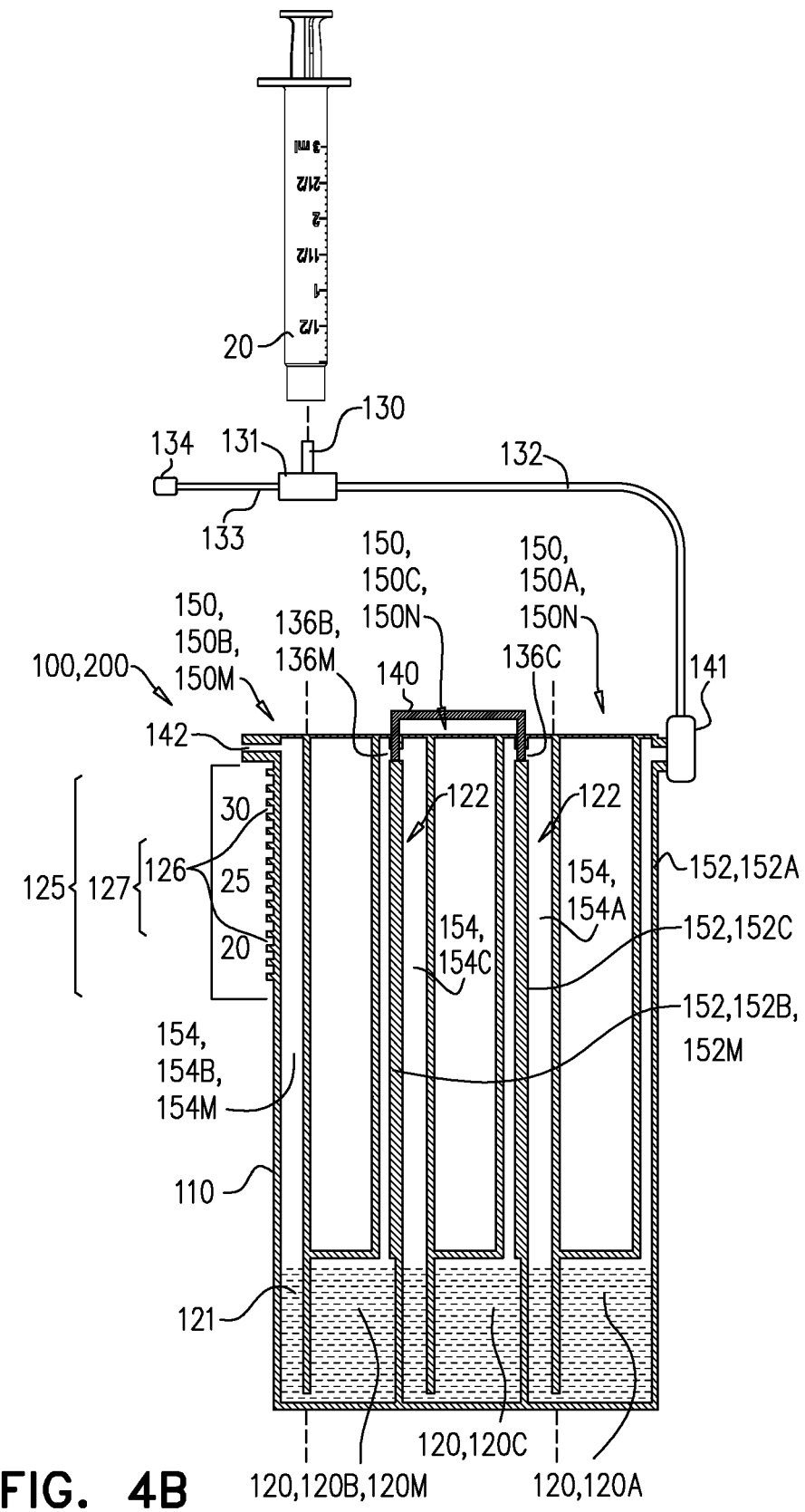

Reference is now made to FIGS. 4A-B, which are schematic illustrations of cuff pressure stabilizer 200 in operational and non-operational states, in accordance with an application of the present invention. The various configurations of cuff pressure stabilizer 100 described herein may optionally implement the techniques of cuff pressure stabilizer 200 described with reference to FIGS. 4A-B. In the operational state, adjacent columnar units 150 are in fluid communication with one another, and upstream-most input port 141 and atmosphere port 142 allow fluid communication therethrough. In the non-operational state, fluid communication is blocked by one or more sealing elements 140 (a) between at least one adjacent pair of columnar units 150, (b) through upstream-most input port 141, and/or (b) through atmosphere port 142. The non-operational state may preserve the location of liquid 121 and/or gas 122 in respective columnar units 150 during storage, transport, and shipping of cuff pressure stabilizer 200, in case the cuff pressure stabilizer is positioned on its side or upside-down, or is shaken.

For some applications, cuff pressure stabilizer 200 is shaped so as to define an intermediate-column input port 136C between output column 154A of upstream-most columnar unit 150A and input column 152C of intermediate columnar unit 150C, and a downstream-column input port 136B between output column 154C of intermediate columnar unit 150C and input column 152B of downstream-most columnar unit 150B. Cuff pressure stabilizer 200 further comprises one or more sealing elements 140, which:

when cuff pressure stabilizer 200 is in the non-operational state, are removably disposed so as to seal intermediate-column input port 136C and downstream-column input port 136B, thereby blocking fluid communication (a) between upstream-most columnar unit 150A and intermediate columnar unit 150C, and (b) between intermediate columnar unit 150C and downstream-most columnar unit 150B, and when cuff pressure stabilizer 200 is in the operational state, are not disposed so as to block the above-mentioned fluid communication.

For some applications, measurement input column 152M is shaped so as to define a measurement-column input port 136M (which is downstream-column input port 136B for configurations in which downstream-most columnar unit 150B is configured to be measurement columnar unit 150M). When cuff pressure stabilizer 200 is in the non-operational state, the one or more sealing elements 140 are removably disposed so as to seal measurement-column input port 136M (and not necessarily intermediate-column input port 136C).

Another configuration of sealing elements 140 is described hereinbelow with reference to FIGS. 12A-C.

For some applications, such as illustrated in FIGS. 1, 2A-B, 3, 5A-B, 6, 7A-B, and 10A-B, cuff pressure stabilizer 100 does not comprise any sealing elements 140. In these applications, cuff pressure stabilizer 100 is always in the operational state (even though it is never in a non-operational state). It is thus to be understood that in the claims, the recitation that the cuff pressure stabilizer is "in an operational state" does not require that cuff pressure stabilizer ever be in a non-operational state, and does not require that the cuff pressure stabilizer comprise any sealing elements.

Reference is still made to FIGS. 1-12C. For some applications, liquid 121 has a density of between 0.8 and 1.2 g/cm3 at 4 degrees Celsius at 1 atm, such as between 0.95 and 1.05 at 4 degrees Celsius at 1 atm. For some applications, liquid 121 comprises at least 50% water by volume, such as at least 90% water by volume. Optionally, liquid 121 comprises a dye to increase the visibility of the liquid for making the pressure measurements.

Reference is still made to FIGS. 1-12C. Typically, cuff pressure stabilizer 100 does not comprise any membranes that block a fluid path between upstream-most input port 141 and atmosphere port 142 when cuff pressure stabilizer 100 is in the operational state. Typically, cuff pressure stabilizer 100 does not comprise a spring for measuring the pressure of gas 122 at upstream-most input port 141 (or at inflation lumen proximal port connector 134, if provided).

Reference is still made to FIGS. 1-12C. Typically, cuff pressure stabilizer 100 is configured to automatically assume the aligned orientation when cuff pressure stabilizer 100 is hung from or otherwise attached to a conventional pole, rail, hospital wall, or other surface or object. For example, cuff pressure stabilizer 100 may comprise a coupling element that is configured to automatically orient the cuff pressure stabilizer in the aligned orientation. The coupling element may comprise a hook or a loop that is hangable from a conventional hook of a conventional pole, similar to the standard hook of IV bags. Alternatively or additionally, the coupling element may comprise a squeezing coupler (e.g., a gripper or a clamp) that is coupleable to a vertical pole (e.g., a vertical IV pole) or a horizontal pole (e.g., a horizontal portion of one of the hooks of the IV pole), or another connector that is configured to be attached to a vertical surface, such as a hospital wall.

Reference is still made to FIGS. 1-12C. For some applications, inflatable cuff 11 of catheter 10 has a volume of between 5 and 25 cc and a largest cross-sectional area, measured in horizontal plane 135, of between 2 and 9 cm2 when inflated to an inflation pressure of 25 cm H2O when not constrained and in atmosphere 99, and when cuff pressure stabilizer 100 is oriented in the aligned orientation, the measurement-column inner cross-sectional area equals between 20% and 80% of the middle cross-sectional area of the inflatable cuff.

Reference is still made to FIGS. 1-12C. For some applications, as shown in the figures and labeled in FIG. 1, respective central longitudinal axes of output columns 154 are perpendicular to horizontal plane 135, when cuff pressure stabilizer 100 is oriented in the aligned orientation. For other applications, the central longitudinal axes are not perpendicular to horizontal plane 135, when cuff pressure stabilizer 100 is oriented in the aligned orientation (configuration not shown).

Reference is still made to FIGS. 1-12C. For some applications, cuff pressure stabilizer 100 further comprises:
- an inflation inlet port 130, which is coupleable with external inflation source 20, such as a syringe;
- a first connector tube 133, which couples inflation lumen proximal port connector 134 in fluid communication with inflation inlet port 130; and
- a second connector tube 132, which couples upstream-most input port 141 in fluid communication with inflation inlet port 130, such that inflation lumen proximal port connector 134 is in fluid communication with upstream-most input port 141 via first connector tube 133 and second connector tube 132.

Typically, inflation inlet port 130 comprises a valve, such as a directional valve. Inflation inlet port 130 isolates the system such there is no exchange of gas (air) between inflatable cuff 11 and atmosphere 99 (ambient air) after initial inflation by external inflation source 20.

For some applications, cuff pressure stabilizer 100 further comprises an inlet junction 131, which comprises inflation inlet port 130, and which couples in fluid communication inflation inlet port 130, first connector tube 133, and second connector tube 132.

Figure 5A:
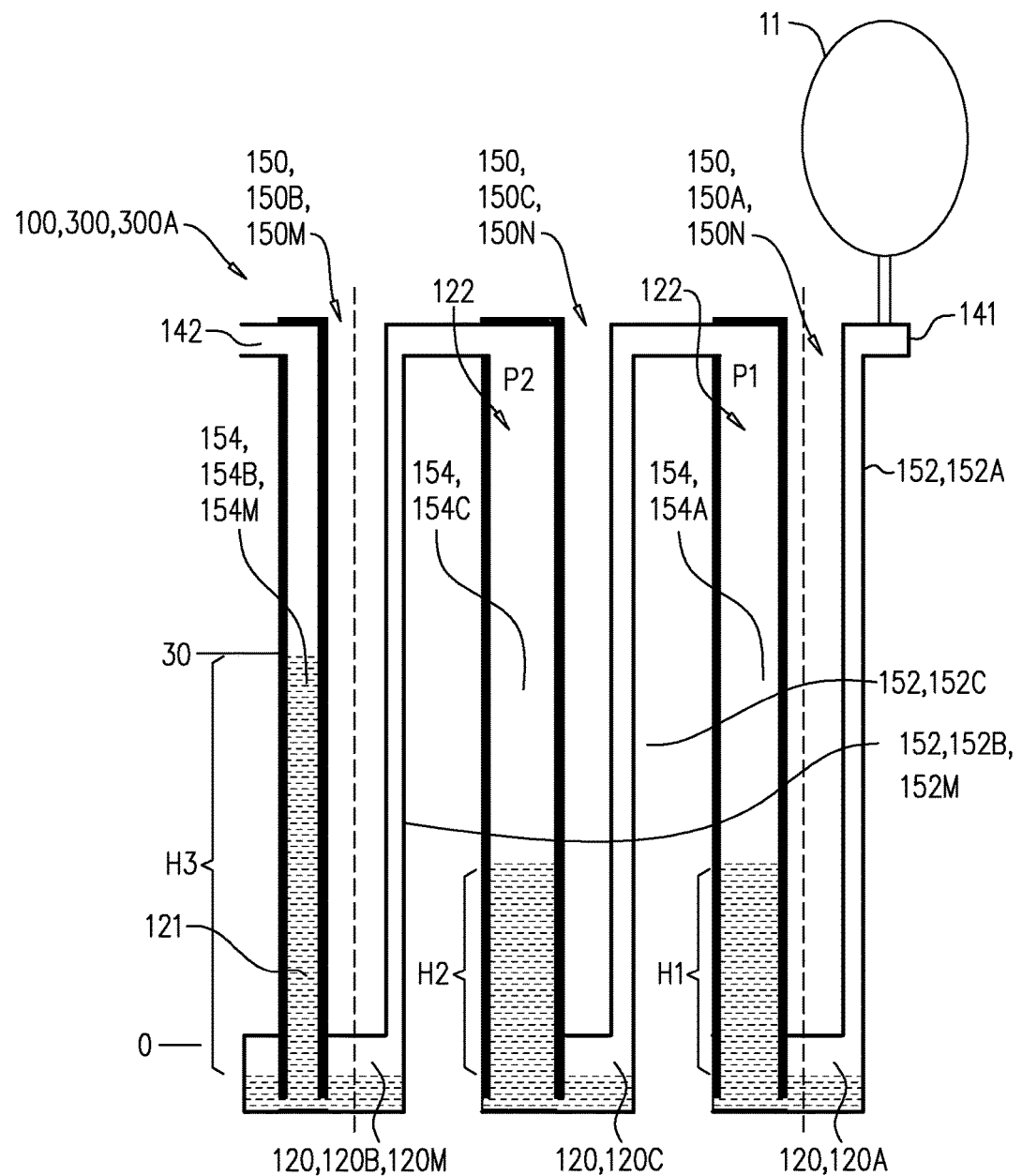
FIGS. 5A-B and 6 are schematic illustrations of respective configurations of another cuff pressure stabilizer, in accordance with respective applications of the present invention.
Figure 5B:
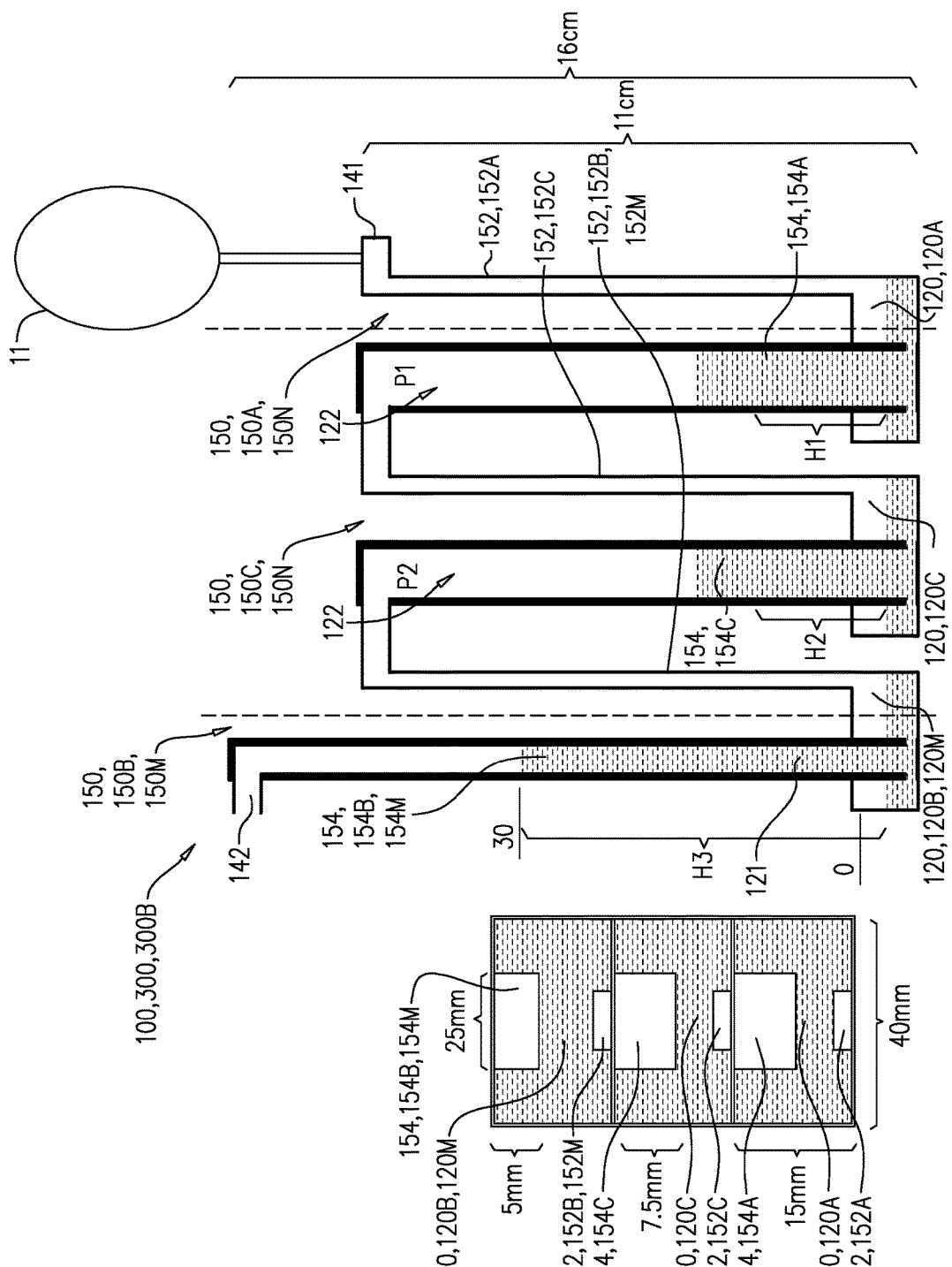
Figure 6:
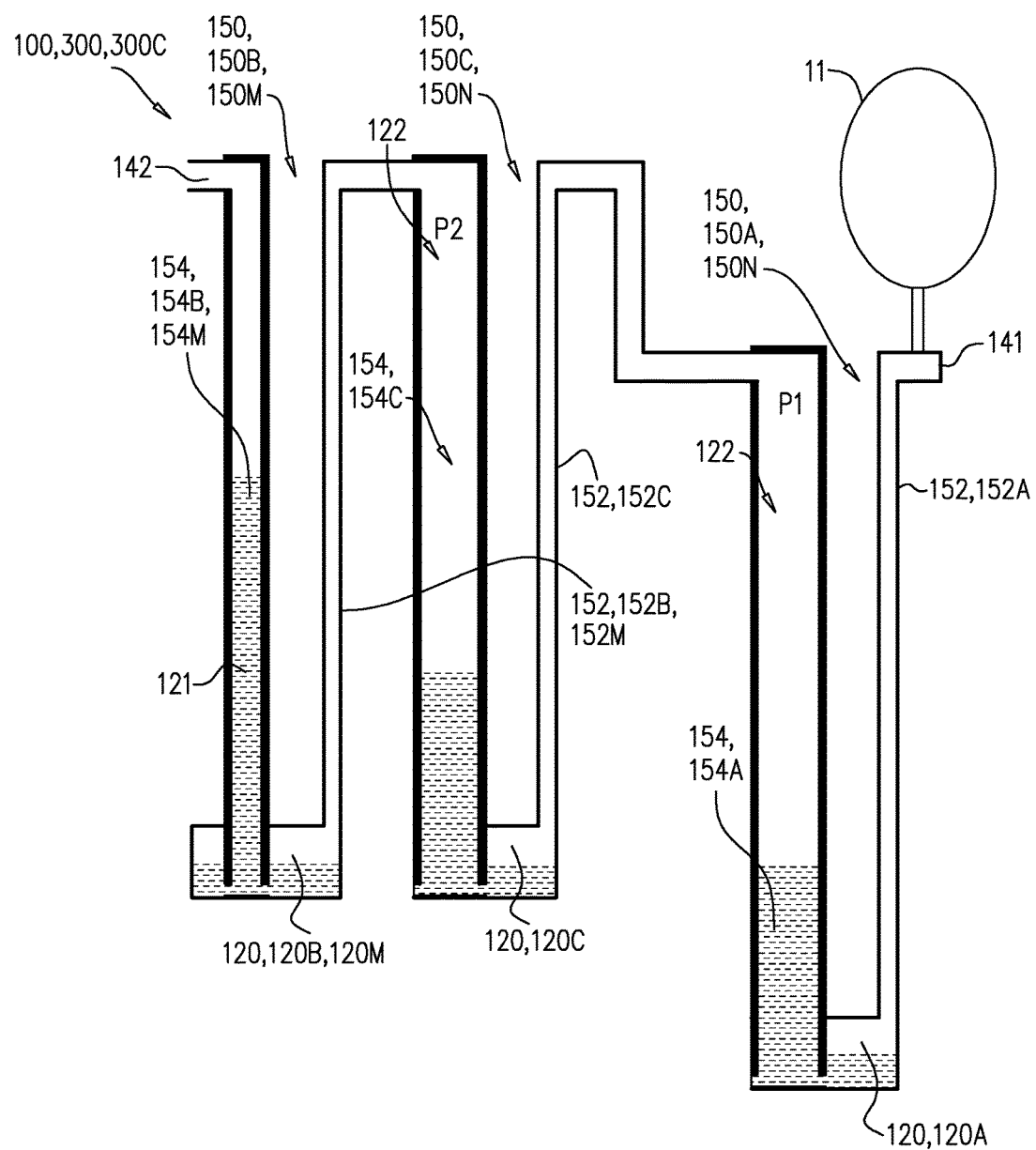

Reference is now made to FIGS. 5A-B and 6, which are schematic illustrations of a cuff pressure stabilizer 300, in accordance with respective applications of the present invention. Cuff pressure stabilizer 300 is one implementation of cuff pressure stabilizer 100, described herein with reference to FIGS. 1-12C, and may implement any of the features thereof.

In cuff pressure stabilizer 300, at least one of (typically, all of) the average target-pressure inner cross-sectional areas of the one or more output columns 154 of the one or more non-measurement columnar units 150N equals at least 120% (e.g., at least 150%, at least 175%, or at least 200%) of the average target-pressure inner cross-sectional area of measurement output column 154M, when cuff pressure stabilizer 300 is oriented in the aligned orientation.

As a result, 1-cm-H2O-indicating pressure indicia markings 126 are farther apart from one another than in the configuration described hereinabove with reference to FIGS. 2A-B.

Reference is made to FIG. 5A, which is a schematic illustration of a cuff pressure stabilizer 300A, which is one exemplary implementation of cuff pressure stabilizer 300. For example, assume the following parameters:
- liquid 121 comprises water,
- cuff pressure stabilizer 300A comprises exactly three columnar units 150 and exactly three corresponding output columns 154,
- cuff pressure stabilizer 300A comprises exactly three fluid reservoirs 120, each of which has a cross-sectional area of 5 cm2, measured in horizontal plane 135,
- the cross-sectional areas of non-measurement output columns 154A and 154C equal 2 cm2, and the cross-sectional area of measurement output column 154M (also labeled 154B) equals 1 cm2, such that the average target-pressure inner cross-sectional areas of the two output columns 154 of the two non-measurement columnar units 150N equals 200% of the average target-pressure inner cross-sectional area of measurement output column 154M, and
- the pressure in inflatable cuff 11 is 30 cm H2O.

Then:

$$H1+H2+H3=30 \text{ cm} \quad \text{(Equation 1)}$$

$$4*H1=30 \text{ cm} \quad \text{(Equation 5)}$$

$$H1=7.5 \text{ cm} \quad \text{(Equation 6)}$$

$$H2=H3=15 \text{ cm} \quad \text{(Equation 7)}$$

Since H1=7.5 cm, pressure P1 of gas 122 in output column 154A of upstream-most columnar unit 150A (and input column 152C of intermediate columnar unit 150C) equals 22.5 cm H2O (7.5 cm H2O less than the 30 cm H2O pressure of inflatable cuff 11). Since H2=7.5 cm, pressure P2 of gas 122 in output column 154C of intermediate columnar unit 150C (and input column 152B of downstream-most columnar unit 150B) equals 15 cm H2O.

The surface level of liquid 121 in each of the three fluid reservoirs 120 goes down:

$$2*7.5 \text{ cm}3/5 \text{ cm}2=3 \text{ cm} \quad \text{(Equation 8)}$$

The vertical distance between 1 cm H2O pressure indicia markings 126 equals:

$$(15 \text{ cm}-3 \text{ cm})/30=\sim0.4 \text{ cm} \quad \text{(Equation 9)}$$

This demonstrates that in some configurations the non-measurement output columns 154 have larger cross-sectional areas than the cross-sectional area of measurement output column 154M, at least in target-pressure range 127 of pressure indicia markings 126 between 23-27 cm H2O, in order to have wider spacing between pressure indicia markings 126 compared with the case of equal cross-sectional area output columns. As described below, this also results in improved suppression of pressure fluctuations.

In order to tolerate a maximum pressure of 36 cm H2O, measurement output column 154M must have a height of at least about 18 cm above the resting surface liquid level at zero pressure (i.e., ambient pressure).

Assuming the above-mentioned parameters, a decrease in volume of inflatable cuff 11 of 1 cc (caused by increased squeezing by the trachea) would increase:
- the surface level of liquid 121 in each of non-measurement output columns 154A and 154C by 0.5 cm,
- the surface level of liquid 121 in measurement output column 154M (also labeled 154B) by 1 cm, and
- thus the pressure in inflatable cuff 11 (as indicated by pressure indicia markings 126) by 2.5 cm H2O, from 25 cm H2O to 27.5 cm H2O, i.e., better suppression of pressure deviation/fluctuation than in the configuration having equal cross-sectional areas of all output columns 154 (discussed above) which gave 28.75 cm H2O under the same volume changes of inflatable cuff 11.

Reference is made to FIG. 5B which is a schematic illustration of a cuff pressure stabilizer 300B, which is one exemplary implementation of cuff pressure stabilizer 300. For example, assume the following parameters:
- liquid 121 comprises water,
- cuff pressure stabilizer 300B comprises exactly three columnar units 150 and exactly three corresponding output columns 154,
- cuff pressure stabilizer 300B comprises exactly three fluid reservoirs 120, each of which has a cross-sectional area of 6 cm2, measured in horizontal plane 135,
- the ratio of cross-sectional areas between the non-measurement output columns 154 and measurement output column 154M is 3:2 (while it was 2:1 in previous examples). Thus the ratio of surface liquid level rise is H1=H2=2/3*H3. In this example, the cross-sectional areas of non-measurement output columns 154A and 154C equal 1.85 cm2, and the cross-sectional area of measurement output column 154M (also labeled 154B) equals 1.25 cm2, such that the average target-pressure inner cross-sectional areas of the two output columns 154 of the two non-measurement columnar units 150N equals 148% of the average target-pressure inner cross-sectional area of measurement output column 154M, and the pressure in inflatable cuff 11 is 30 cm H2O.
Then:

$$H1+H2+H3=30 \text{ cm} \quad \text{(Equation 1)}$$

$$7/3*H3=30 \text{ cm} \quad \text{(Equation 10)}$$

$$H3=\sim 12.8 \text{ cm} \quad \text{(Equation 11)}$$

$$H2=H1=\sim 8.6 \text{ cm} \quad \text{(Equation 12)}$$

Since H1=8.6 cm, pressure P1 of gas 122 in output column 154A of upstream-most columnar unit 150A (and input column 152C of intermediate columnar unit 150C) equals 21.4 cm H2O. Since H2=8.6 cm, pressure P2 of gas 122 in output column 154C of intermediate columnar unit 150C (and input column 152B of downstream-most columnar unit 150B) equals 12.8 cm H2O.

The surface level of liquid 121 in each of the three fluid reservoirs 120 goes down approximately:

$$1.85*8.6 \text{ cm}3/6 \text{ cm}2 = 2.65 \text{ cm} \quad \text{(Equation 13)}$$

The vertical distance between 1 cm H2O pressure indicia markings 126 equals:

$$(12.8 \text{ cm}-2.65 \text{ cm})/30=\sim 0.34 \text{ cm} \quad \text{(Equation 14)}$$

In order to tolerate a maximum pressure of 36 cm H2O, measurement output column 154M must have a height of at least about 18 cm above the resting surface liquid level at zero pressure (i.e., ambient pressure).

Assuming the above-mentioned parameters, a decrease in volume of inflatable cuff 11 of 1 cc (caused by increased squeezing by the trachea) would increase:
  the surface level of liquid 121 in measurement output column 154M (also labeled 154B) by 1/1.25=0.8 cm, and
  thus the pressure in inflatable cuff 11 (as indicated by pressure indicia markings 126) by 0.8/0.34=2.3 cm H2O, from 25 cm H2O to 27.3 cm H2O.
Therefore, the combination of larger cross-sectional areas and non-equal cross-sectional areas of measurement output column 154M and non-measurement columns 154N results in enhancement of pressure fluctuation attenuation due to volume change of inflatable cuff 11.

As shown in the cross-sectional views in FIG. 5B, by way of example and not limitation:
  each of three fluid reservoirs 120 has the following dimensions: 1.5 cm width*4 cm length (i.e., cross-section 6 cm2)*3.5 cm depth;
  measurement output column 154M (also labeled 154B) has a cross-sectional area of 1.25 cm2 (5 mm*25 mm) and a height of 12 cm; and
  each of non-measurement output columns 154A and 154C has a cross-sectional area of 1.85 cm2 (7.5 mm*25 mm) and a height of 12 cm.
This is thus an implementation of the example discussed above.

Reference is again made to FIGS. 1-12C, and is additionally made to FIG. 6, which is a schematic illustration of a cuff pressure stabilizer 300C, which is another exemplary implementation of cuff pressure stabilizer 300. For some applications, output column 154A of the upstream-most columnar unit 150A is disposed at least partially alongside output column 154B of downstream-most columnar unit 150B for a distance of at least 3 cm, such as at least 5 cm, e.g., at least 10 cm, measured vertically when cuff pressure stabilizer 100 is oriented in the aligned orientation.

For some applications, output column 154A of upstream-most columnar unit 150A is disposed entirely alongside output column 154B of downstream-most columnar unit 150B (and entirely alongside output column 154C of intermediate columnar unit 150C and any other intermediate columnar units that may be provided), along the entire lengths of the output columns, such as shown in FIGS. 1, 2A-B, 3, 4A-B, 5A-B, 7A-B, 8A-B, and 10A-B. However, such an arrangement is not necessary. The relative axial positions and axial overlap of columnar units 150, including of output columns 154 and input columns 152, does not affect the function of cuff pressure stabilizer 100. In fact, each of columnar units 150 may be placed independently of one another, so long as there is fluid communication between the columnar units. For example, as shown in FIG. 6, output column 154A of the upstream-most columnar unit 150A is disposed only partially alongside, rather than entirely alongside, output column 154B of downstream-most columnar unit 150B.

In addition, columnar units 150, including of output columns 154 and input columns 152, need not have the same axial lengths. For example, measurement output column 154M is shown as being longer than non-measurement columns 154N in FIGS. 6 and 9.

Figure 7A:
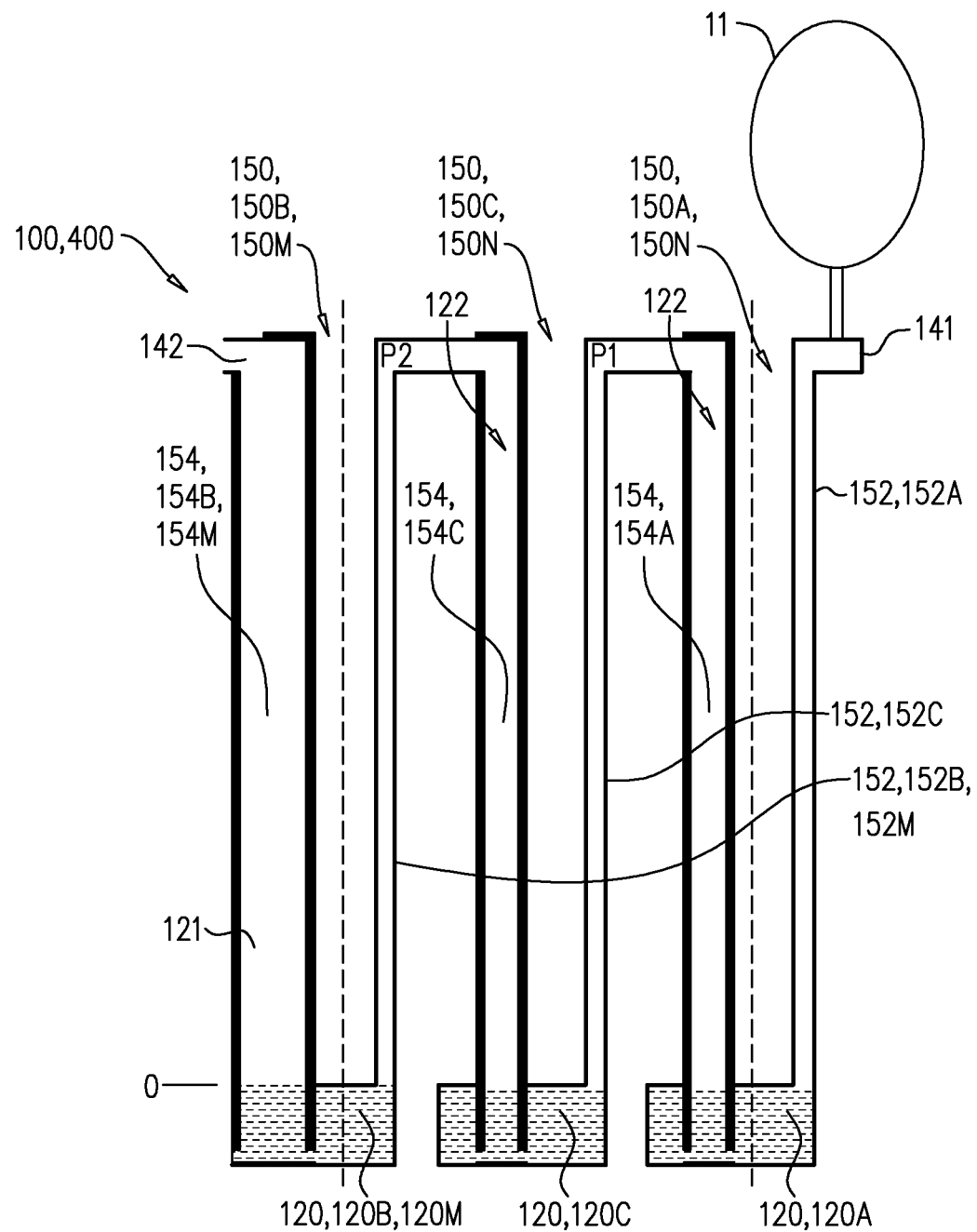
FIGS. 7A-B are schematic illustrations of yet another cuff pressure stabilizer in resting and pressurized states, respectively, in accordance with an application of the present invention.
Figure 7B:
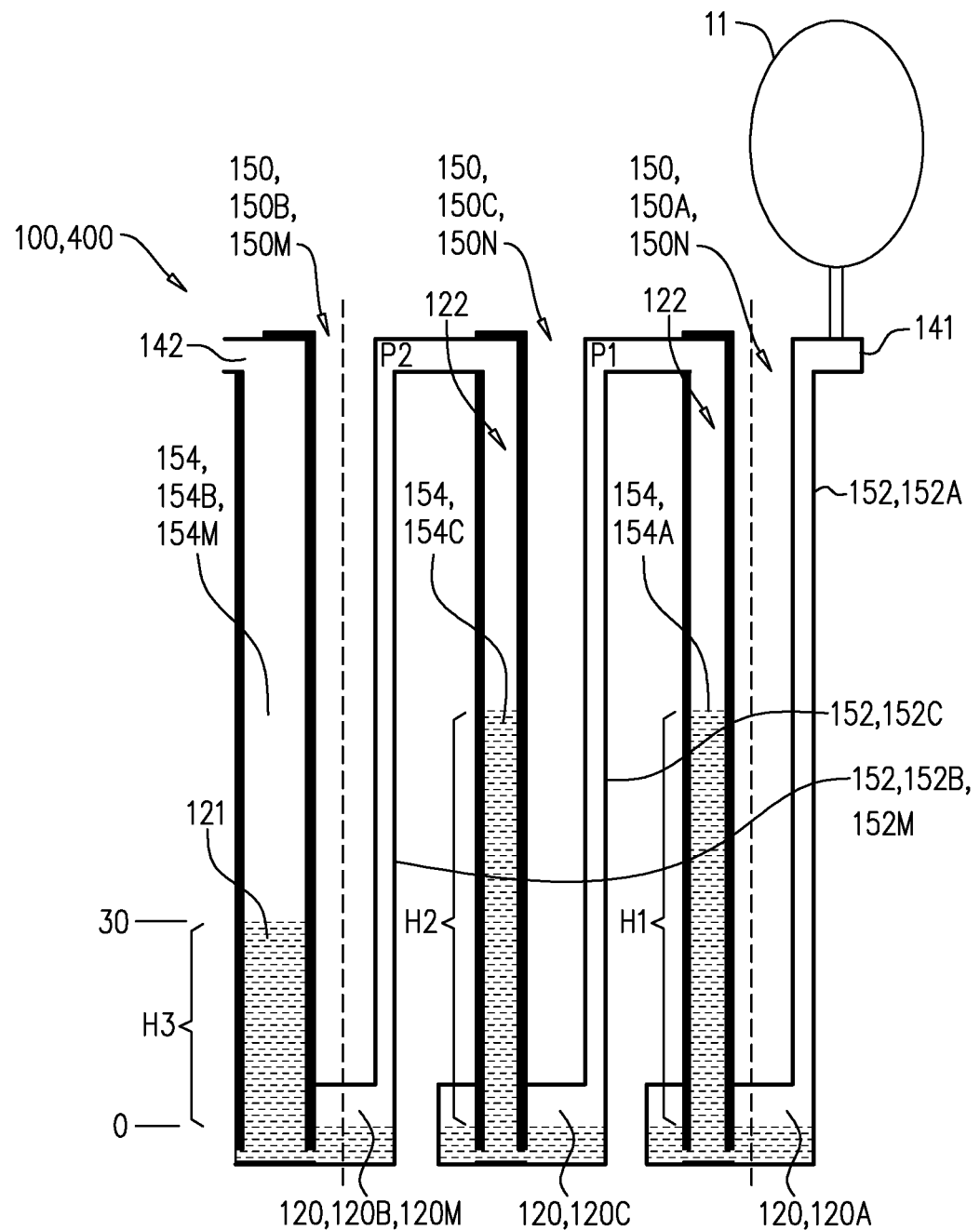

Reference is now made to FIGS. 7A-B, which are schematic illustrations of a cuff pressure stabilizer 400 in resting and pressurized states, respectively, in accordance with an application of the present invention. Cuff pressure stabilizer 400 is one implementation of cuff pressure stabilizer 100, described herein with reference to FIGS. 1-12C, and may implement any of the features thereof.

In cuff pressure stabilizer 400, at least one of (typically, all of) the average target-pressure inner cross-sectional areas of the one or more output columns 154 of the one or more non-measurement columnar units 150N equals no more than 90%, (e.g., no more than 75%, no more than 60%, or no more than 50%) of the average target-pressure inner cross-sectional area of measurement output column 154M, when cuff pressure stabilizer 400 is oriented in the aligned orientation.

As mentioned above, FIG. 7A shows cuff pressure stabilizer 400 in a resting state, in which the pressure of atmosphere 99 is 1 atm, inflatable cuff 11 is inflated to 1 atm, and the surface level of liquid 121 is the same in all output columns 154. As the pressure increases in inflatable cuff 11 from the resting state to a pressurized state, shown in 7B, liquid 121 rises in output columns 154, and goes down in fluid reservoirs 120. The resulting height differences between output columns 154 and their respective fluid reservoirs 120 are labeled H1, H2, and H3 for output column 154A of upstream-most columnar unit 150A, output column 154C of intermediate columnar unit 150C, and output column 154B of downstream-most columnar unit 150B, respectively.

Reference is made to FIG. 7B. For example, assume the following parameters:
  liquid 121 comprises water,
  cuff pressure stabilizer 400 comprises exactly three columnar units 150 and exactly three corresponding output columns 154.
  cuff pressure stabilizer 400 comprises exactly three fluid reservoirs 120, each of which has a cross-sectional area of 5 cm2, measured in horizontal plane 135,
  the cross-sectional areas of non-measurement output columns 154A and 154C equal 1 cm2, and the cross-sectional area of measurement output column 154M (also labeled 154B) equals 2 cm2, such the average target-pressure inner cross-sectional areas of the two output columns 154 of the two non-measurement columnar units 150N equals 50% of the average target-pressure inner cross-sectional area of measurement output column 154M, and the pressure in inflatable cuff 11 is 30 cm H2O.
Then:

$$H1+H2+H3=30 \text{ cm} \quad \text{(Equation 1)}$$

$$H1=H2=2*H3 \quad \text{(Equation 15)}$$

$$5*H3=30 \text{ cm} \quad \text{(Equation 16)}$$

$$H1=H2=12 \text{ cm} \quad \text{(Equation 17)}$$

$$H3=6 \text{ cm} \quad \text{(Equation 18)}$$

Since H1=12 cm, pressure P1 of gas 122 in output column 154A of upstream-most columnar unit 150A (and input column 152C of intermediate columnar unit 150C) equals 18 cm H2O. Since H2=12 cm, pressure P2 of gas 122 in output column 154C of intermediate columnar unit 150C (and input column 152B of downstream-most columnar unit 150B) equals 6 cm H2O.

The surface level of liquid 121 in each of the three fluid reservoirs 120 goes down:

$$12 \text{ cm3/5 cm2}=2.4 \text{ cm} \quad \text{(Equation 19)}$$

The vertical distance between 1 cm H2O pressure indicia markings 126 equals:

$$(6 \text{ cm}-2.4 \text{ cm})/30=\sim 0.1 \text{ cm} \quad \text{(Equation 20)}$$

Such vertical separation pressure indicia markings 126 may be too dense for practical reading from a distance by a human, so such configurations may not be suitable for practical use.

Figure 8A:
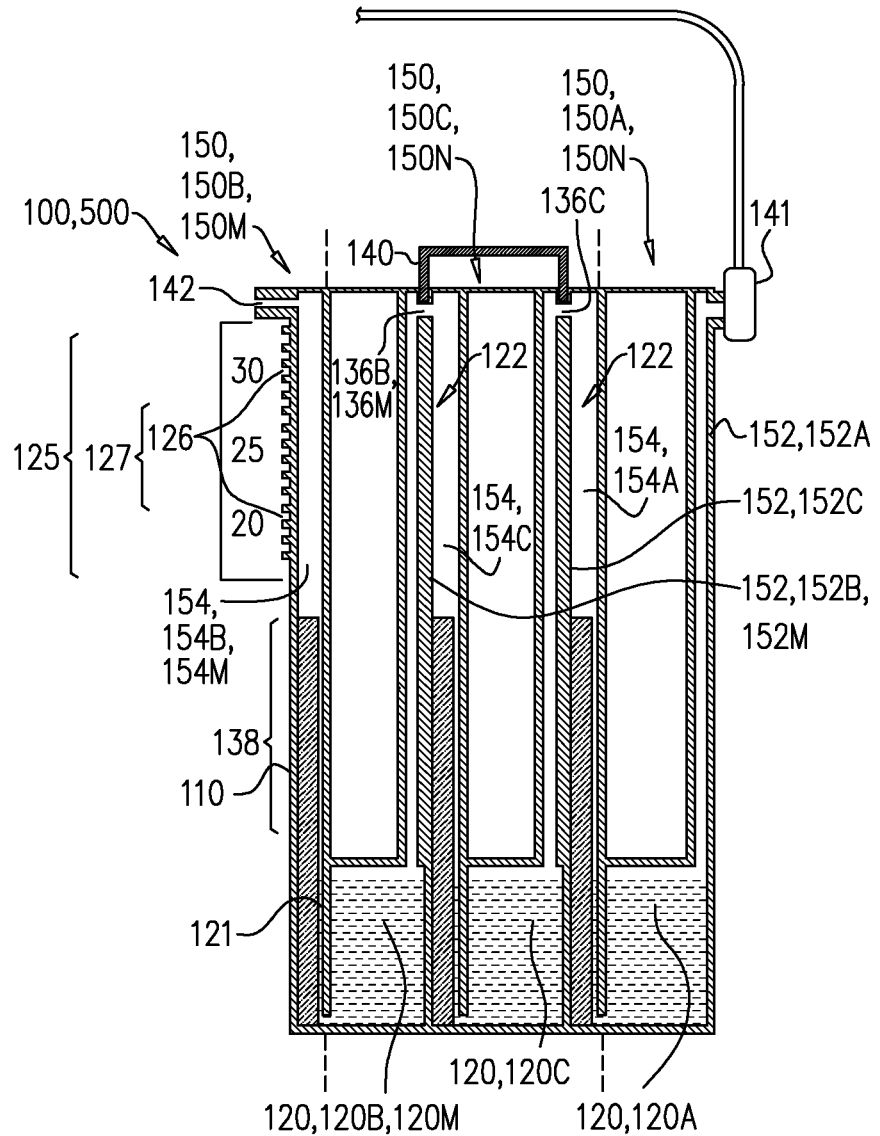
FIGS. 8A-B are schematic illustrations of still another cuff pressure stabilizer in resting and pressurized states, respectively, in accordance with an application of the present invention.
Figure 8B:
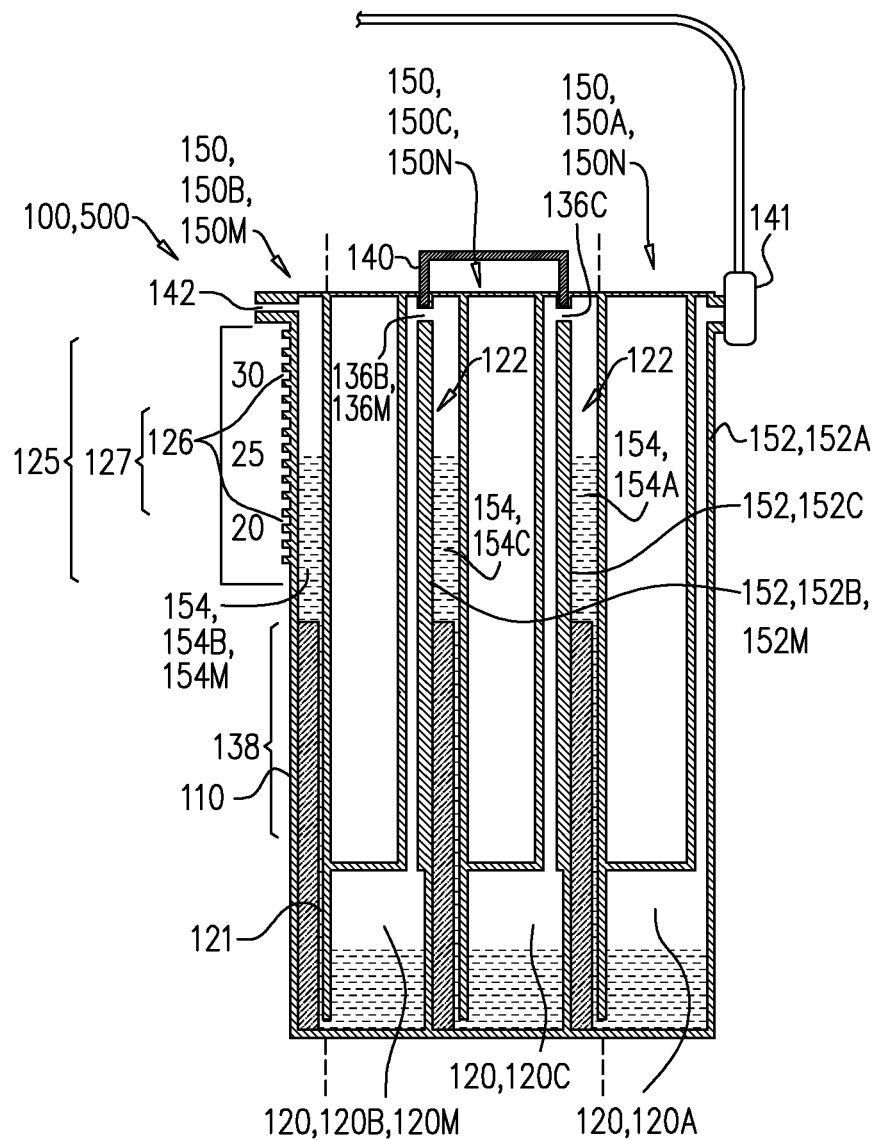

Reference is now made to FIGS. 8A-B, which are schematic illustrations of a cuff pressure stabilizer 500 in resting and pressurized states, respectively, in accordance with an application of the present invention. Cuff pressure stabilizer 500 is one implementation of cuff pressure stabilizer 100, described herein with reference to FIGS. 1-12C, and may implement any of the features thereof.

When cuff pressure stabilizer 500 is oriented in the aligned orientation:
  output columns 154 have respective average low-pressure inner cross-sectional areas,
  each of the average low-pressure inner cross-sectional areas is measured in horizontal plane 135 at all axial locations along the respective output column 154 that correspond to respective pressures of gas 122 at upstream-most input port 141 (and also at inflation lumen proximal port connector 134, if provided) in a low pressure range 138 of between 5 and 15 cm H2O, and
  for each of output columns 154, the average target-pressure inner cross-sectional area thereof equals at least 200% (e.g., at least 400%, at least 500%, or at least 6006') of the average low-pressure inner cross-sectional area thereof.

The narrower portions of output columns 154 in low pressure range 138 reduce the total required amount of liquid 121, which may reduce the total weight of cuff pressure stabilizer 500 compared to configurations in which the narrower portions are not provided.

For some applications, the average low-pressure inner cross-sectional areas of the different output columns 154 equal or approximately equal one another, such as shown in FIGS. 8A-B.

Figure 9:
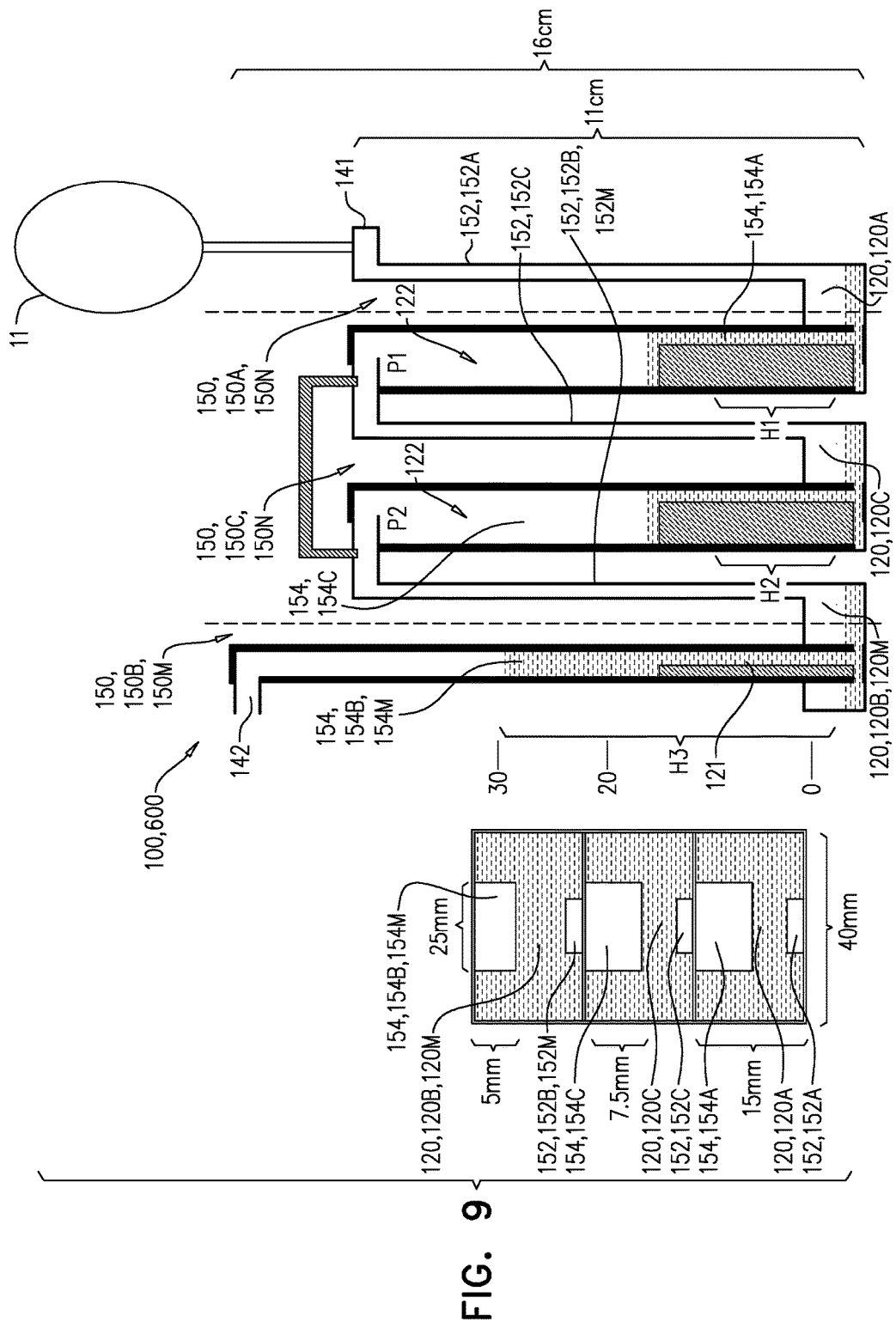
FIG. 9 is a schematic illustration of another cuff pressure stabilizer, in accordance with an application of the present invention.

Reference is now made to FIG. 9, which is a schematic illustration of a cuff pressure stabilizer 600, in accordance with an application of the present invention. Cuff pressure stabilizer 600 is one implementation of cuff pressure stabilizer 100, described herein with reference to FIGS. 1-12C, and may implement any of the features thereof. Cuff pressure stabilizer 600 combines the features of cuff pressure stabilizer 300, described hereinabove with reference to FIGS. 5A-B and 6, and cuff pressure stabilizer 500, described hereinabove with reference to FIGS. 8A-B.

For example, assume the following parameters:
  liquid 121 comprises water,
  cuff pressure stabilizer 600 comprises exactly three columnar units 150 and exactly three corresponding output columns 154,
  cuff pressure stabilizer 600 comprises exactly three fluid reservoirs 120, each of which has a cross-sectional area of 6 cm2, measured in horizontal plane 135.
  the cross-sectional areas of non-measurement output columns 154A and 154C equal 3 cm2, and the cross-sectional area of measurement output column 154M (also labeled 154B) equals 2 cm2, such that the average target-pressure inner cross-sectional areas of the two output columns 154 of the two non-measurement columnar units 150N equals 150% of the average target-pressure inner cross-sectional area of measurement output column 154M.

This is again an example of a 3:2 ratio of (i) the respective average target-pressure inner cross-sectional areas of non-measurement output columns 154 of non-measurement columnar units 150N to (ii) the average target-pressure inner cross-sectional area of measurement output column 154M, with fluid reservoirs 120, each of which has a cross-sectional area of 6 cm2. Hence all the calculations of the previously discussed example apply. The narrow cross-sections at the lower portion of output columns 154 do not affect the measurements and fluctuation attenuation effect in the range 20 cm H2O to 30 cm H2O.

For some applications, the average low-pressure inner cross-sectional areas of the different output columns 154 equal or approximately equal one another, such as shown in FIG. 9. Alternatively, for some applications (configuration not shown), the average low-pressure inner cross-sectional area of measurement output column 154M in low pressure range 138 is greater than the respective average low-pressure inner cross-sectional areas of non-measurement output columns 154 of non-measurement columnar units 150N in low pressure range 138. For example, (a) a ratio of (i) the average low-pressure inner cross-sectional area of measurement output column 154M to (ii) the respective average low-pressure inner cross-sectional areas of non-measurement output columns 154 may equal (b) a ratio of (i) the respective average target-pressure inner cross-sectional areas of non-measurement output columns 154 to (ii) the average target-pressure inner cross-sectional area of measurement output column 154M. For example, in the exemplary configuration of FIG. 9 modified as just described, both of these ratios would be 3:2.

Figure 10A:
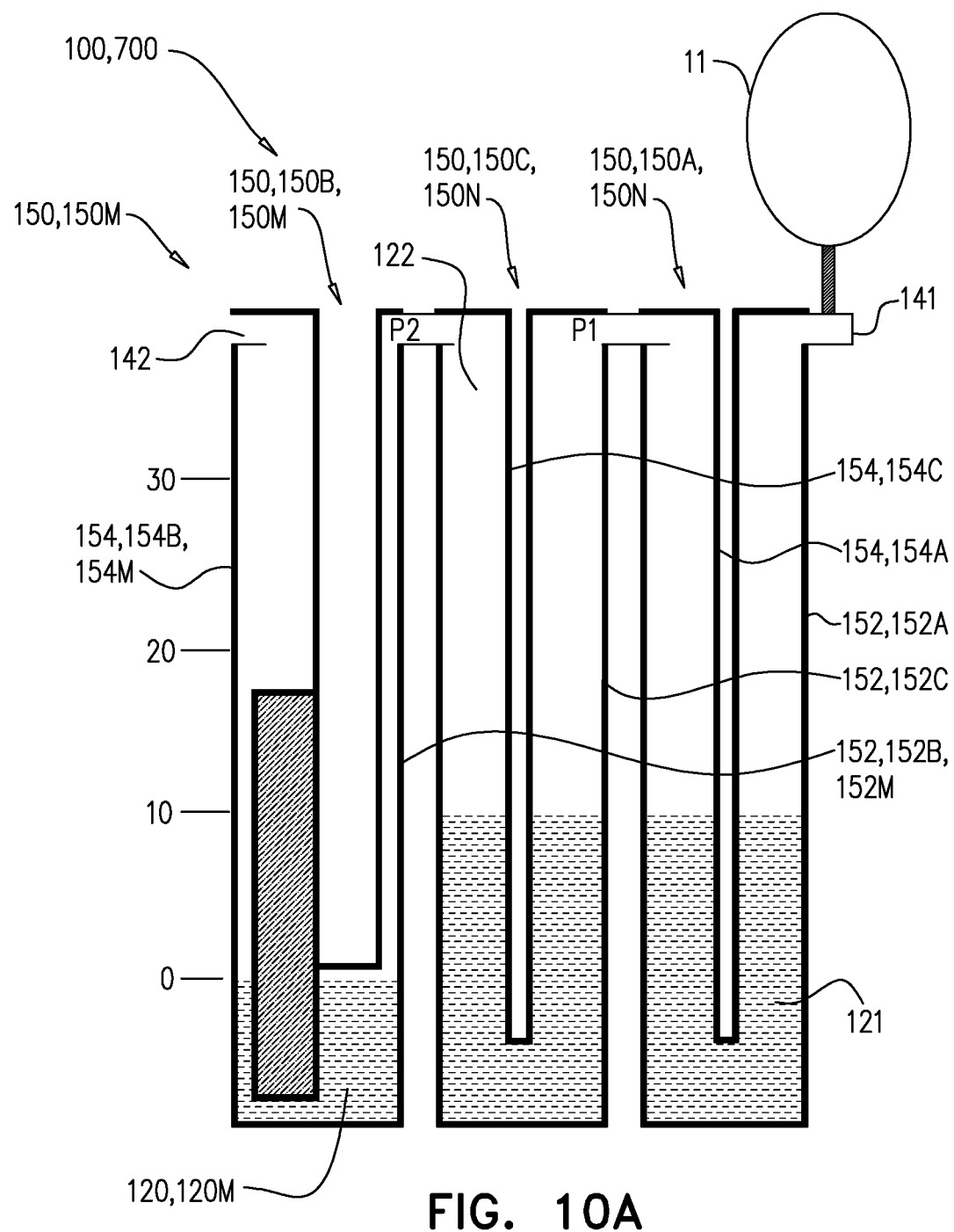
FIGS. 10A-B are schematic illustrations of yet another cuff pressure stabilizer in resting and pressurized states, respectively, in accordance with an application of the present invention.
Figure 10B:
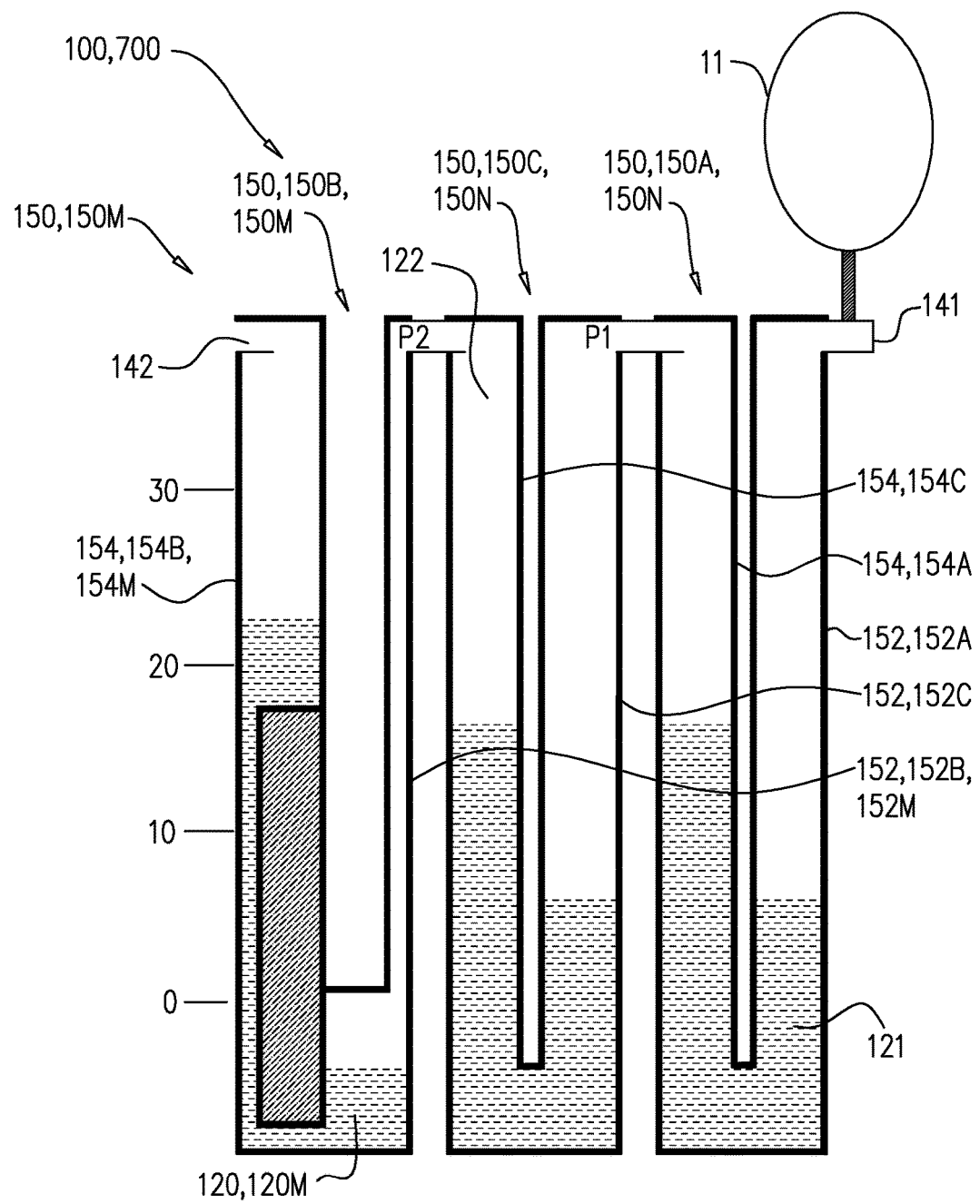

Reference is now made to FIGS. 10A-B, which are schematic illustrations of a cuff pressure stabilizer 700 in resting and pressurized states, respectively, in accordance with an application of the present invention. Cuff pressure stabilizer 700 is one implementation of cuff pressure stabilizer 100, described herein with reference to FIGS. 1-12C, and may implement any of the features thereof.

In this configuration, only measurement columnar unit 150M comprises a fluid reservoir 120 (measurement fluid reservoir 120M), and the one or more non-measurement columnar units 150N do not comprise fluid reservoirs. In the illustrated configuration, by way of example, in other respects cuff pressure stabilizer 700 has the properties and configuration of cuff pressure stabilizer 400, described hereinabove with reference to FIGS. 7A-B in combination with those of cuff pressure stabilizer 600, described hereinabove with reference to FIG. 9.

Reference is now made to FIGS. 11A-F, which are schematic illustrations of a cuff pressure stabilizer 800, in accordance with an application of the present invention. Cuff pressure stabilizer 800 is one implementation of cuff pressure stabilizer 100, described herein with reference to FIGS. 1-12C, and may implement any of the features thereof. The configurations described hereinabove are illustrated as linear arrangements of the columns. However, these illustrations are for illustrative clarity only and are not meant to be limiting. For example, FIGS. 11A-F illustrate an implementation of columnar units 150 with a circular arrangement of the columns in 3D space.

Figure 12C:
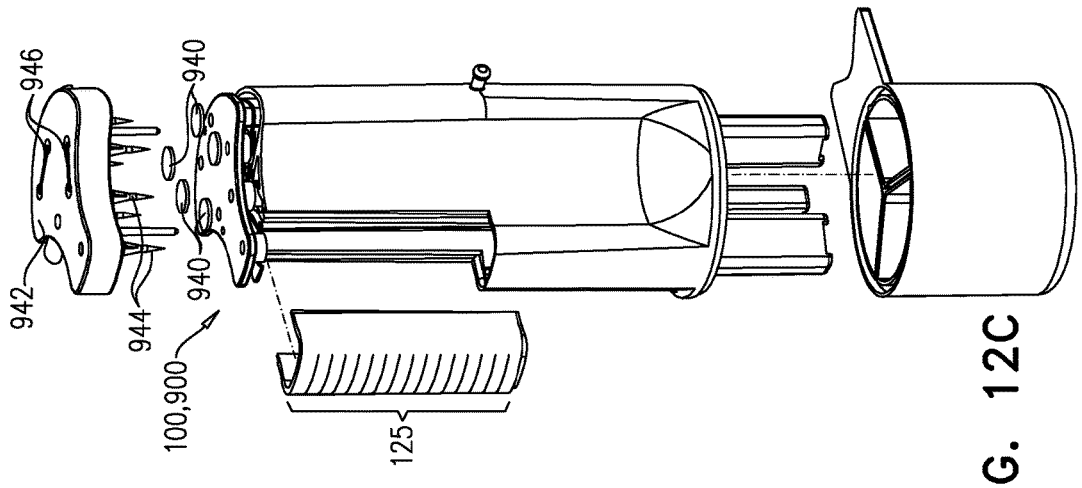
FIGS. 12A-C are schematic illustrations of another cuff pressure stabilizer, in accordance with an application of the present invention.
Figure 12B:
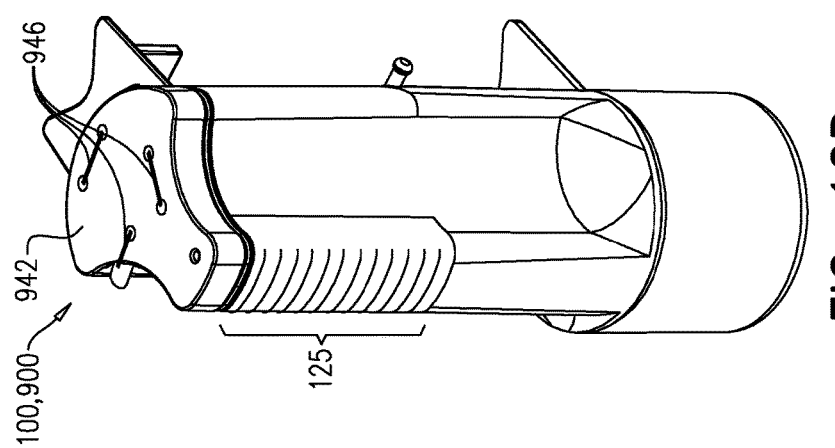
Figure 12A:
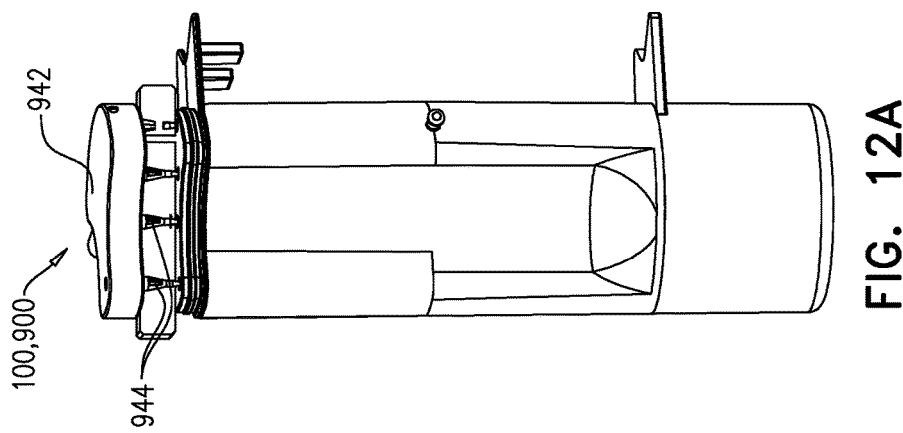

Reference is now made to FIGS. 12A-C, which are schematic illustrations of a cuff pressure stabilizer 900, in accordance with an application of the present invention. FIGS. 12A and 12B show cuff pressure stabilizer 900 in non-operational and operational states, respectively, and FIG. 12C shows cuff pressure stabilizer 900 partially disassembled. Cuff pressure stabilizer 900 is one implementation of cuff pressure stabilizer 100, described herein with reference to FIGS. 1-12C, and may implement any of the features thereof, likewise, the various configurations of cuff pressure stabilizer 100 described herein may optionally implement the techniques of cuff pressure stabilizer 900.

When cuff pressure stabilizer 900 is in the non-operational state, in fluid communication between adjacent columnar units 150 is blocked, and upstream-most input port 141 and atmosphere port 142 are blocked, such as for storage, transport and shipping of cuff pressure stabilizer 900. When cuff pressure stabilizer 900 is in the operational state, adjacent columnar units 150 are in fluid communication with one another, and upstream-most input port 141 and atmosphere port 142 allow fluid communication therethrough.

For some applications, cuff pressure stabilizer 900 comprises sealing elements 940 (which, for example, comprise thin membranes), which block fluid communication (a) between at least one adjacent pair of columnar units 150, (b) through upstream-most input port 141, and/or (b) through atmosphere port 142 (labeled in other figures. For example, sealing elements 940 may be disposed at the top of cuff pressure stabilizer 900 and columnar units 150. For some applications, cuff pressure stabilizer 900) comprises a cover element 942 that comprises sharp piercing elements 944. In order to transition cuff pressure stabilizer 900 from the non-operational state to the operational state, a user presses cover element 942 down against the top of columnar units 150, which causes sharp piercing elements 944 to puncture sealing elements 940 (e.g., membranes), thereby enabling fluid communication between adjacent pairs of columnar units 150, through upstream-most input port 141, and through atmosphere port 142.

For some applications, cover element 942 further comprises one or more fluid-communication channels 946, and sharp piercing elements 944 comprise sharp piercing needles, interiors of pairs of which are in fluid communication with fluid-communication channels 946, respectively. When the user presses cover element 942 down against the top of columnar units 150, the sharp piercing units puncture sealing elements 940 (e.g., membranes) and enable fluid communication between adjacent pairs of columnar units 150 via respective fluid-communication channels 946, and optionally (a) between downstream-most columnar unit 150B and atmosphere port 142 and/or (b) between upstream-most columnar unit 150A and upstream-most input port 141.

Although cuff pressure stabilizers 100, 200, 300, 500, 600, 700, 800, and 900 have been described as being used with inflatable cuff 11 of catheter 10, cuff pressure stabilizers 100, 200, 300, 500, 600, 700, 800, and 900 may alternatively be used with other inflatable chambers of other medical devices or non-medical devices. For example, the inflatable chamber may be a Foley catheter balloon, a gastric balloon, a balloon of colonoscope, or a balloon of an endoscope.

In the description and claims of the present application, each of the verbs, "comprise," "include" and "have," and conjugates thereof, are used to indicate that the object or objects of the verb are not necessarily a complete listing of members, components, elements or parts of the subject or subjects of the verb. The articles "a" and "an" are used herein to refer to one or to more than one (i.e., to at least one) of the grammatical object of the article. By way of example, "an element" means one element or more than one element. The term "including" is used herein to mean, and is used interchangeably with, the phrase "including but not limited to." The term "or" is used herein to mean, and is used interchangeably with, the term "and/or," unless context clearly indicates otherwise. The term "such as" is used herein to mean, and is used interchangeably, with the phrase "such as but not limited to."

All publications, patent applications, patents, and other references mentioned herein are incorporated by reference in their entirety. In case of conflict, the present patent specification, including definitions, will prevail. In addition, the materials, methods, and examples are illustrative only and not intended to be limiting.

For brevity, some explicit combinations of various features are not explicitly illustrated in the figures and/or described. It is now disclosed that any combination of the method or device features disclosed herein can be combined in any manner—including any combination of features—any combination of features can be included in any embodiment and/or omitted from any embodiments.

As used in the present application, including in the claims, a "fluid" comprises liquid and/or gas.

Although applications of the present invention have generally been described as for use with a tracheal ventilation tube, they may also be used with other catheters 10, such as tracheostomy catheters.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

US Provisional Application 62/305,567, filed Mar. 9, 2016

U.S. Provisional Application 62/402,024, filed Sep. 30, 2016

US Provisional Application 62/405,115, filed Oct. 6, 2016

U.S. Provisional Application 62/448,254, filed Jan. 19, 2017

International Application PCT/IL2017/050284, filed Mar. 8, 2017, which published as PCT Publication WO 2017/153988

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A cuff pressure stabilizer for use in contact with the atmosphere of the Earth and for use with a catheter having an inflatable cuff, an inflation lumen, and an inflation lumen proximal port, the cuff pressure stabilizer comprising:
    two or more columnar units;
    one or more seals, wherein the cuff pressure stabilizer is configured to be in (a) a sealed state when the one or more seals block fluid communication between at least one adjacent pair of the columnar units, and (b) a non-sealed state when the one or more seals do not block the fluid communication between the at least one adjacent pair of the columnar units, wherein the columnar units:
        comprise (a) respective input columns and (b) respective output columns, wherein the respective output columns (i) are disposed at least partially alongside the respective input columns, and (ii) are configured to be in fluid communication with the respective input columns when the cuff pressure stabilizer is in the non-sealed state, and
        include (a) an upstream-most columnar unit and (b) a downstream-most columnar unit;
    a liquid; and
    a gas,
    wherein the input column of the upstream-most columnar unit is shaped so as to define an upstream-most input port, which is coupleable in fluid communication with the inflation lumen proximal port of the catheter,
    wherein the output column of the downstream-most columnar unit is shaped so as to define an atmosphere port that is configured to be open to the atmosphere when the cuff pressure stabilizer is in the non-sealed state,
    wherein the output column of the upstream-most columnar unit is disposed at least partially alongside the output column of the downstream-most columnar unit,
    wherein the two or more columnar units are arranged, when the cuff pressure stabilizer is in the non-sealed state, so as to define a fluid communication path from the upstream-most input port, to the input column of the upstream-most columnar unit, to the output column of the upstream-most columnar unit, to the input column of the downstream-most columnar unit, to the output column of the downstream-most columnar unit, and to the atmosphere port,
    wherein one of the columnar units is configured as a measurement columnar unit, which comprises a plurality of pressure indicia markings distributed along the measurement columnar unit,
    wherein the cuff pressure stabilizer is configured such that when the cuff pressure stabilizer is in the non-sealed state and is oriented in an aligned orientation in which the pressure indicia markings reflect, to within 1 cm H2O, respective pressures of gas at the upstream-most input port at least in a target-pressure range of 23 to 27 cm H2O:
        all of the output columns have respective average target-pressure inner cross-sectional areas, each of the average target-pressure inner cross-sectional areas measured in a horizontal plane at all axial locations along the respective output column that correspond to the respective pressures of the gas at the upstream-most input port in the target-pressure range, and
        each of the average target-pressure inner cross-sectional areas is between 0.5 and 4 cm2, and
    wherein the cuff pressure stabilizer is configured such that when the cuff pressure stabilizer is in the non-sealed state and is oriented in the aligned orientation and the pressure of the gas at the upstream-most input port falls in the target-pressure range:
        the liquid is contained at least partially in all of the output columns, and
        the gas is contained at least partially in the input column of the downstream-most columnar unit and at least partially in the output column of the upstream-most columnar unit.

2. The cuff pressure stabilizer according to claim 1,
    wherein the measurement input column of the measurement columnar unit is shaped so as to define a measurement fluid reservoir,
    wherein the measurement output column is shaped so as to define an inlet that is disposed entirely within the measurement fluid reservoir,
    wherein the cuff pressure stabilizer is configured such that when the cuff pressure stabilizer is in the non-sealed state, the measurement input column is in fluid communication with the inlet of the measurement output column via the measurement fluid reservoir, and
    wherein the cuff pressure stabilizer is configured such that when the cuff pressure stabilizer is in the non-sealed state and the gas at the upstream-most input port is at atmospheric pressure, the liquid is contained partially in the measurement fluid reservoir and partially in the measurement output column, and a volume of the liquid in the measurement fluid reservoir is greater than a volume of the liquid in the measurement output column.

3. The cuff pressure stabilizer according to claim 2, wherein the cuff pressure stabilizer is configured such that when the cuff pressure stabilizer is in the non-sealed state and is oriented in the aligned orientation:
    an average inner cross-sectional area of the measurement fluid reservoir, measured in the horizontal plane between upper and lower height end-points, equals at least 200% of an average relevant-pressure inner cross-sectional area of the measurement output column, measured in the horizontal plane at all axial locations along the measurement output column that correspond to respective pressures of the gas at the upstream-most input port in a relevant-pressure range of 0 to 30 cm H2O,
    the upper height end-point is at a height that corresponds to a pressure of the gas at the upstream-most input port equal to the atmospheric pressure, and
    the lower height end-point is at a height of a highest point at which there is fluid communication between the measurement output column and the measurement input column.

4. The cuff pressure stabilizer according to claim 2, wherein the cuff pressure stabilizer is configured such that a distance between a highest point of the measurement output column and a lowest point of the measurement fluid reservoir is between 12 and 24 cm, when the cuff pressure stabilizer is oriented in the aligned orientation.

5. The cuff pressure stabilizer according to claim 2, wherein a volume of the measurement fluid reservoir is at least 2 cc.

6. The cuff pressure stabilizer according to claim 2, wherein the cuff pressure stabilizer is configured such that when the cuff pressure stabilizer is in the non-sealed state and the gas at the upstream-most input port is at the atmospheric pressure, a volume of the liquid in the measurement fluid reservoir is less than a volume of the measurement output column.

7. The cuff pressure stabilizer according to claim 1, wherein the cuff pressure stabilizer is configured such that when the cuff pressure stabilizer is in the non-sealed state and the gas at the upstream-most input port is at atmospheric pressure, for at least one of the columnar units, the liquid is contained partially in the input column and partially in the output column of the columnar unit, and a volume of the liquid in the input column of the columnar unit is less than a volume of the output column of the columnar unit.

8. The cuff pressure stabilizer according to claim 1, wherein the cuff pressure stabilizer is configured such that when the cuff pressure stabilizer is in the non-sealed state and the gas at the upstream-most input port is at atmospheric pressure, for all of the columnar units, the liquid is contained partially in the input column and partially in the output column of the columnar units, and respective volumes of the liquid in the respective input columns of the columnar units are less than respective volumes of the respective output columns of the columnar units.

9. The cuff pressure stabilizer according to claim 1,
wherein one or more of the columnar units, other than the measurement columnar unit, are configured as one or more non-measurement columnar units, respectively, and
wherein the cuff pressure stabilizer is configured such that at least one of the average target-pressure inner cross-sectional areas of the one or more output columns of the one or more non-measurement columnar units equals at least 120% of the average target-pressure inner cross-sectional area of the measurement output column, when the cuff pressure stabilizer is oriented in the aligned orientation.

10. The cuff pressure stabilizer according to claim 9, wherein the cuff pressure stabilizer is configured such that each of the average target-pressure inner cross-sectional areas of the one or more output columns of the one or more non-measurement columnar units equals at least 120% of the average target-pressure inner cross-sectional area of the measurement output column, when the cuff pressure stabilizer is oriented in the aligned orientation.

11. The cuff pressure stabilizer according to claim 9, wherein the cuff pressure stabilizer is configured such that when the cuff pressure stabilizer is in the non-sealed state, the liquid is contained partially in the one or more non-measurement columnar units, and the liquid in the one or more non-measurement columnar units is obscured from viewing from outside the cuff pressure stabilizer at least in the target-pressure range.

12. The cuff pressure stabilizer according to claim 1, wherein the cuff pressure stabilizer is configured such that the input column of the measurement columnar unit contains a portion of the gas at all pressures of the gas at the upstream-most input port in a relevant-pressure range between 0 and 30 cm H2O, when the cuff pressure stabilizer is in the non-sealed state and is oriented in the aligned orientation.

13. The cuff pressure stabilizer according to claim 1, wherein the cuff pressure stabilizer is configured such that the output column of the upstream-most columnar unit is disposed at least partially alongside the output column of the downstream-most columnar unit for a distance of at least 3 cm, measured vertically when the cuff pressure stabilizer is oriented in the aligned orientation.

14. The cuff pressure stabilizer according to claim 1, wherein the downstream-most columnar unit is configured as the measurement columnar unit.

15. The cuff pressure stabilizer according to claim 1, wherein the cuff pressure stabilizer is configured such that, for each of the output columns, an inner cross-sectional area thereof, measured in the horizontal plane, is between 0.5 and 4 cm2 at all axial locations along the output column that correspond to respective pressures of the gas at the upstream-most input port in the target-pressure range, when the cuff pressure stabilizer is in the non-sealed state and is oriented in the aligned orientation.

16. The cuff pressure stabilizer according to claim 1, wherein the cuff pressure stabilizer is configured such that each of the average target-pressure inner cross-sectional areas is at least 1 cm2.

17. The cuff pressure stabilizer according to claim 1,
wherein the two or more columnar units comprise three or more columnar units, which include (i) the upstream-most columnar unit, (ii) the downstream-most columnar unit, and (iii) at least an intermediate columnar unit,
wherein one of the (i) the upstream-most columnar unit, (ii) the downstream-most columnar unit, and (iii) at least an intermediate columnar unit is configured as the measurement columnar unit, and
wherein the cuff pressure stabilizer is configured such that when the cuff pressure stabilizer is in the non-sealed state, the three or more columnar units are arranged so as to define the fluid communication path from the upstream-most input port, to the input column of the upstream-most columnar unit, to the output column of the upstream-most columnar unit, to the input column of the intermediate columnar unit, to the output column of the intermediate columnar unit, to the input column of the downstream-most columnar unit, to the output column of the downstream-most columnar unit, and to the atmosphere port.

18. The cuff pressure stabilizer according to claim 1,
wherein the input column of the measurement columnar unit is shaped so as to define a measurement-column input port, and
wherein the cuff pressure stabilizer is configured to be in the sealed state when the one or more seals block the fluid communication through the measurement-column input port.

19. The cuff pressure stabilizer according to claim 1, wherein the cuff pressure stabilizer is configured such that when the cuff pressure stabilizer is oriented in the aligned orientation:
the output columns have respective average low-pressure inner cross-sectional areas,
each of the average low-pressure inner cross-sectional areas is measured in the horizontal plane at all axial locations along the respective output column that correspond to respective pressures of the gas at the upstream-most input port in a low pressure range of between 5 and 15 cm H2O, and for each of the output columns, the average target-pressure inner cross-sectional area thereof equals at least 200% of the average low-pressure inner cross-sectional area thereof.

20. The cuff pressure stabilizer according to claim 1, wherein the cuff pressure stabilizer further comprises an inflation lumen proximal port connector, which is shaped to form an air-tight seal with the inflation lumen proximal port of the catheter, and wherein the cuff pressure stabilizer is configured such that when the cuff pressure stabilizer is in the non-sealed state, the upstream-most input port is in fluid communication with the inflation lumen proximal port connector such that the upstream-most input port is coupleable in fluid communication with the inflation lumen proximal port of the catheter via the inflation lumen proximal port connector.

21. The cuff pressure stabilizer according to claim 20, wherein the inflation lumen proximal port connector comprises a male conical fitting with a taper.

22. The cuff pressure stabilizer according to claim 1, wherein the liquid has a density of between 0.8 and 1.2 g/cm3 at 4 degrees Celsius at 1 atm.

23. The cuff pressure stabilizer according to claim 1, wherein the liquid comprises at least 50% water by volume.

24. The cuff pressure stabilizer according to claim 1, wherein the catheter is a tracheal ventilation tube, and wherein the cuff pressure stabilizer is for use with the tracheal ventilation tube.

25. The cuff pressure stabilizer according to claim 1, wherein the cuff pressure stabilizer does not comprise any membranes that block a fluid path between the upstream-most input port and the atmosphere port when the cuff pressure stabilizer is in the non-sealed state.

26. The cuff pressure stabilizer according to claim 1, wherein the cuff pressure stabilizer does not comprise a spring for measuring the pressure of the gas at the inflation lumen proximal port connector.

27. A system comprising the cuff pressure stabilizer according to claim 1, wherein the system further comprises the catheter, which comprises the inflatable cuff, the inflation lumen, and the inflation lumen proximal port.

28. The cuff pressure stabilizer according to claim 1, wherein the one or more seals comprise membranes that block the fluid communication between the at least one adjacent pair of the columnar units when the cuff pressure stabilizer is in the sealed state, wherein the cuff pressure stabilizer further comprises piercing elements, and wherein the cuff pressure stabilizer is configured to transition from the sealed state to the non-sealed state when the piercing elements puncture the membranes such that the membranes do not block the fluid communication between the at least one adjacent pair of the columnar units.

29. A method for use in contact with the atmosphere of the Earth and for use with a catheter having an inflatable cuff, an inflation lumen, and an inflation lumen proximal port, the method comprising:

providing a cuff pressure stabilizer, which comprises (A) two or more columnar units; (B) one or more seals, wherein the cuff pressure stabilizer is configured to be in (a) a sealed state when the one or more seals block fluid communication between at least one adjacent pair of the columnar units, and (b) a non-sealed state when the one or more seals do not block the fluid communication between the at least one adjacent pair of the columnar units, wherein the columnar units: (a) comprise (i) respective input columns and (ii) respective output columns, wherein the respective output columns (1) are disposed at least partially alongside the respective input columns, and (2) are configured to be in fluid communication with the respective input columns when the cuff pressure stabilizer is in the non-sealed state, and (b) include (i) an upstream-most columnar unit and (ii) a downstream-most columnar unit; (C) a liquid; and (D) a gas; and coupling the upstream-most input port in fluid communication with the inflation lumen proximal port of the catheter, wherein the input column of the upstream-most columnar unit is shaped so as to define an upstream-most input port, which is coupleable in fluid communication with the inflation lumen proximal port of the catheter, wherein the output column of the downstream-most columnar unit is shaped so as to define an atmosphere port that is configured to be open to the atmosphere when the cuff pressure stabilizer is in the non-sealed state, wherein the output column of the upstream-most columnar unit is disposed at least partially alongside the output column of the downstream-most columnar unit, wherein the two or more columnar units are arranged, when the cuff pressure stabilizer is in the non-sealed state, so as to define a fluid communication path from the upstream-most input port, to the input column of the upstream-most columnar unit, to the output column of the upstream-most columnar unit, to the input column of the downstream-most columnar unit, to the output column of the downstream-most columnar unit, and to the atmosphere port, wherein one of the columnar units is configured as a measurement columnar unit, which comprises a plurality of pressure indicia markings distributed along the measurement columnar unit, wherein the cuff pressure stabilizer is configured such that when the cuff pressure stabilizer is in the non-sealed state and is oriented in an aligned orientation in which the pressure indicia markings reflect, to within 1 cm H2O, respective pressures of gas at the upstream-most input port at least in a target-pressure range of 23 to 27 cm H2O:

all of the output columns have respective average target-pressure inner cross-sectional areas, each of the average target-pressure inner cross-sectional areas measured in a horizontal plane at all axial locations along the respective output column that correspond to respective pressures of the gas at the upstream-most input port in the target-pressure range, and each of the average target-pressure inner cross-sectional areas is between 0.5 and 4 cm2, and wherein the cuff pressure stabilizer is configured such that when the cuff pressure stabilizer is in the non-sealed state and is oriented in the aligned orientation and the pressure of the gas at the upstream-most input port falls in the target-pressure range:

the liquid is contained at least partially in all of the output columns, and the gas is contained at least partially in the input column of the downstream-most columnar unit and at least partially in the output column of the upstream-most columnar unit.

* * * * *